United States Patent
Draetta et al.

(10) Patent No.: US 6,251,585 B1
(45) Date of Patent: *Jun. 26, 2001

(54) ASSAY AND REAGENTS FOR IDENTIFYING ANTI-PROLIFERATIVE AGENTS

(75) Inventors: Giulio Draetta, Winchester; Guillaume Cottarel, Chestnut Hill; Veronique Damagnez, Cambridge, all of MA (US)

(73) Assignee: Mitotix, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/428,762

(22) Filed: Apr. 24, 1995

Related U.S. Application Data

(63) Continuation of application No. 08/073,383, filed on Jun. 4, 1993, now Pat. No. 5,443,962.

(51) Int. Cl.[7] .............................. C12Q 1/68; C12Q 1/42; C12Q 1/02; G01N 33/53
(52) U.S. Cl. .............................. 435/6; 435/7.31; 435/21; 435/29; 435/32; 435/254.11; 435/254.2
(58) Field of Search .............................. 435/6, 7.31, 21, 435/29, 32, 254.11, 254.2

(56) References Cited

U.S. PATENT DOCUMENTS

| | | | |
|---|---|---|---|
| 5,262,409 | 11/1993 | Margolis et al. | 514/183 |
| 5,294,538 | * 3/1994 | Beach | 435/21 |
| 5,441,880 | * 8/1995 | Beach et al. | 435/193 |
| 5,443,962 | * 8/1995 | Draetta et al. | 435/29 |

FOREIGN PATENT DOCUMENTS

| | | |
|---|---|---|
| WO 92/20796 | 11/1992 | (WO). |
| WO 93/06123 | 4/1993 | (WO). |
| WO 93/10242 | 5/1993 | (WO). |
| WO 93/19176 | 9/1993 | (WO). |

OTHER PUBLICATIONS

Coleman et al. "Negative Regulation of the Wee 1 Protein Kinase by Direct Action of the Nim1/Cdr1 Mitotic Inducer" *Cell* 72:919,929, 1993.

Hoffman et al. "Phosphorylation and Activation of Human cdc–25–C by cdc2–cyclin B and its Involvement in the Self–Amplification of MPF at Mitosis." *The Embo. Journal* 12:53–63, 1993.

Murray A.W. "Creative Blocks: Cell–Cycle Checkpoints and Feedback Controls" *Nature Review* Article, 359:599–604, 1992.

Parker et al. "Inactivation of the p34cdc2–Cyclin B Complex by the Human WEE 1 Tyrosine Kinase" *Science* 257:1995–1957, 1992.

Andreassen et al. "2–Aminopurine Overrides Multiple Cell Cycle Checkpoints in BHK Cells" *PNAS* 89:2272–2276, 1992.

Rowley et al. "The WEE1 Protein Kinase is Required for Radiation–Induced Mitotic Delay" *Nature* Letters, 356:353–355, 1992.

Subramani et al. "Checkpoint Controls in Schizosaccharomyces pombe: rad1" *The Embo. Journal* 11:1335–1342, 1992.

Ducommun et al. "Cdc2 Phosphorylation is Required for its Interaction with Cyclin" *The Embo. Journal* 10:3311–3319, 1991.

Dunphy et al. "The cdc25 Protein Contains an Intrinsic Phosphatase Activity" *Cell* 67:189–196, 1991.

Gautier et al. "Cdc25 is a Specific Tyrosine Phosphatase that Directly Activates p34cdc2" *Cell* 67:197–211, 1991.

Steinmann et al. "Chemically Induced Premature Mitosis: Differential Response in Rodent and Human Cells and the Relationship to Cyclin B Synthesis and p34cdc2/cyclin B Complex Formation" *PNAS* 88:6843–6847, 1991.

Lundgren et al. "Mik1 and wee1 Cooperate in the Inhibitory Tyrosine Phosphorylation of cdc2" *Cell* 64:1111–1122, 1991.

Galactioniv et al. "Specific Activation of cdc25 Tyrosine Phosphatases by B–Type Cyclins: Evidence for Multiple Roles of Mitotic Cyclins" *Cell* 67:1181–1194, 1991.

Osmani et al. "Activation of the nimA Protein Kinase Plays a Unique Role During Mitosis that Cannot be Bypassed by Absence of the bimE Checkpoint" *The Embo. Journal* 10:2669–2679, 1991.

Railet et al. "A New Screening Test for Antimitotic Compounds Using the Universal M Phase–Specific Protein Kinase p34cdc2/cyclin Bcdc13, Affinity–Immobilized on p13suc1–Coated Microtitration Plates" *Anticancer Research* 11:1581–1590, 1991.

(List continued on next page.)

*Primary Examiner*—Ponnathapu Achutamurthy
*Assistant Examiner*—Peter P. Tung
(74) *Attorney, Agent, or Firm*—Foley, Hoag & Eliot LLP; Matthew P. Vincent; David P. Halstead

(57) ABSTRACT

The present invention makes available assays and reagents for identifying anti-proliferative agents, such as mitotic and meiotic inhibitors. The present assay provides a simple and rapid screening test which relies on scoring for positive cellular proliferation as indicative of anti-mitotic or anti-meiotic activity, and comprises contacting a candidate agent with a cell which has an impaired cell-cycle checkpoint and measuring the level of proliferation in the presence and absence of the agent. The checkpoint impairment is such that it either causes premature progression of the cell through at least a portion of a cell-cycle or inhibition of normal progression of the cell through at least a portion of a cell-cycle, but can be off-set by the action of an agent which inhibits at least one regulatory protein of the cell-cycle in a manner which counter-balances the effect of the impairment.

25 Claims, 8 Drawing Sheets

OTHER PUBLICATIONS

Andreassan et al. "Induction of Partial Mitosis in BHK Cells by 2–aminpurine" *Journal of Cell Science* 100:299–310, 1991.

D'Urso et al. "Cell Cycle Control of DNA Replication by a Homologue from Human Cells of the—34cdc2 Protein Kinase" *Science* 250:786–791, 1990.

Enoch et al. "Mutation of Fission Yeast Cell Cycle Control Genes Abolishes Dependence of Mitosis on DNA Replication" *Cell* 60:665–673, 1990.

Brizuela et al. P13suc1 Acts in the Fission Yeast Cell Division Cycle as a Component of the p34cdc2 Protein Kinase: *The Embo. Journal* 6:3507–3514, 1987.

Russell et al. "The Mitotic Inducer nim1+ Functions in a REgulatory Network of Protein Kinase Homologs Controlling the Initiation of Mitosis" *Cell* 49:569–576, 1987.

Lau et al. "Mechanism by which Caffeine Potentiates Lethality of Nitrogen Mustard" *PNAS* 79:2942–2946, 1982.

Masui, Biochem. Cell Biol. 70:920–945 (1992).

Munder et al., Mol. Gen. Genet. 214:271–277 (1988).

Baratte et al., Anticancer Res. 12:873–880 (1992).

Ausubel et al. (eds.), Short Protocols in Molecular Biology, 2nd edition, John Wiley & Sons, Inc., New York, NY, pp. 6–1 to 6–2, 1992.*

Russell et al., Cell 45:145–153 1986.*

* cited by examiner

ASSAY AND REAGENTS FOR IDENTIFYING ANTI-PROLIFERATIVE AGENTS

This application is a continuation of application Ser. No. 08/073,383 filed on Jun. 4, 1993 now U.S. Pat. No. 5,443, 962. The contents of the aforementioned application are hereby incorporated by reference.

BACKGROUND OF THE INVENTION

Entry of cells into mitosis characteristically involves coordinated and simultaneous events, which include, for example, cytoskeletal rearrangements, disassembly of the nuclear envelope and of the nucleoli, and condensation of chromatin into chromosomes. Cell-cycle events are thought to be regulated by a series of interdependent biochemical steps, with the initiation of late events requiring the successful completion of those preceding them. In eukaryotic cells mitosis does not normally take place until the G1, S and G2 phases of the cell-cycle are completed. For instance, at least two stages in the cell cycle are regulated in response to DNA damage, the G1/S and the G2/M transitions. These transitions serve as checkpoints to which cells delay cell-cycle progress to allow repair of damage before entering either S phase, when damage would be perpetuated, or M phase, when breaks would result in loss of genomic material. Both the G1/S and G2/M checkpoints are known to be under genetic control as there are mutants that abolish arrest or delay which ordinarily occur in wild-type cells in response to DNA damage.

The progression of a proliferating eukaryotic cell through the cell-cycle checkpoints is controlled by an array of regulatory proteins that guarantee that mitosis occurs at the appropriate time. These regulatory proteins can provide exquisitely sensitive feedback-controlled circuits that can, for example, prevent exit of the cell from S phase when a fraction of a percent of genomic DNA remains unreplicated (Dasso et al. (1990) Cell 61:811–823) and can block advance into anaphase in mitosis until all chromosomes are aligned on the metaphase plate (kieder et al. (1990) J. Cell Biol. 110:81–95). In particular, the execution of various stages of the cell-cycle is generally believed to be under the control of a large number of mutually antagonistic kinases and phosphatases. For example, genetic, biochemical and morphological evidence implicate the cdc2 kinase as the enzyme responsible for triggering mitosis in eukaryotic cells (for reviews, see Hunt (1989) Curr. Opin. Cell Biol. 1:268–274; Lewin (1990) Cell 61:743–752; and Nurse (1990) Nature 344:503–508). The similarities between the checkpoints in mammalian cells and yeast have suggested similar roles for cdc protein kinases across species. In support of this hypothesis, a human cdc2 gene has been found that is able to substitute for the activity of an S. pombe cdc2 gene in both its G1/S and G2/M roles (Lee et al (1987) Nature 327:31). Likewise, the fact that the cdc2 homolog of S. cerevisae (cdc28) can be replaced by the human cdc2 also emphasizes the extent to which the basic cell-cycle machinery has been conserved in evolution.

As mitosis progresses, the cdc2 kinase appears to trigger a cascade of downstream mitotic phenomena such as metaphase alignment of chromosomes, segregation of sister chromatids in anaphase, and cleavage furrow formation. Many target proteins involved in mitotic entry of the proliferating cell are directly phosphorylated by the cdc2 kinase. For instance, the cdc2 protein kinase acts by phosphorylating a wide variety of mitotic substrates such as nuclear lamins, histones, and microtubule-associated proteins (Moreno et al. (1990) Cell 61:549–551; and Nigg (1991) Semin. Cell Biol. 2:261–270). The cytoskeleton of cultured cells entering mitosis is rearranged dramatically. Caldesmon, an actin-associated protein, has also been shown to be a cdc2 kinase substrate (Yamashiro et al. (1991) Nature 349:169–172), and its phosphorylation may be involved in induction of M-phase-specific dissolution of actin cables. The interphase microtubule network disassembles, and is replaced by a mitosis-specific astral array emanating from centrosomes. This rearrangement has been correlated with the presence of mitosis-specific cdc2 kinase activity in cell extracts (Verde et al (1990) Nature 343:233–238). Changes in nuclear structure during mitotic entry are also correlated with cdc2 kinase activity. Chromatin condensation into chromosomes is accompanied by cdc2 kinase-induced phosphorylation of histone H1 (Langan et al. (1989) Molec. Cell. Biol. 9:3860–3868), nuclear envelope dissolution is accompanied by cdc2-specific phosphorylation of lamin B (Peter et al. (1990) Cell 61:591–602) nucleolar disappearance is coordinated with the cdc2-dependent phosphorylation of nucleolin and NO38.

The activation of cdc2 kinase activity occurs during the M phase and is an intricately regulated process involving the concerted binding of an essential regulatory subunit (i.e., a cyclin) and phosphorylation at multiple, highly conserved positions (for review, see Fleig and Gould (1991) Semin. Cell Biol. 2:195–204). The complexity of this activation process most likely stems from the fact that, as set out above, the initiation of mitosis must be keyed into a number of signal transduction processes whose function is to guard against the inappropriate progression of the cell-cycle. In particular, the cell employs such signaling mechanisms to guarantee that mitosis and cytokinesis do not occur unless cellular growth and genome duplication have occurred in an accurate and timely manner.

The cdc2 kinase is subject to multiple levels of control. One well-characterized mechanism regulating the activity of cdc2 involves the phosphorylation of tyrosine, threonine, and serine residues; the phosphorylation level of which varies during the cell-cycle (Draetta et al. (1988) Nature 336:738–744; Dunphy et al. (1989) Cell 58:181–191; Morla et al. (1989) Cell 58:193–203; Gould et al. (1989) Nature 342:39–45; and Solomon et al. (1990) Cell 63:1013–1024). The phosphorylation of cdc2 on Tyr-15 and Thr-14, two residues located in the putative ATP binding site of the kinase, negatively regulates kinase activity. This inhibitory phosphorylation of cdc2 is mediated at least impart by the wee1 and mik1 tyrosine kinases (Russel et al. (1987) Cell 49:559–567; Lundgren et al. (1991) Cell 64:1111–1122; Featherstone et al. (1991) Nature 349:808–811; and Parker et al. (1992) PNAS 89:2917–2921). These kinases act as mitotic inhibitors, over-expression of which causes cells to arrest in the G2 phase of the cell-cycle. By contrast, loss of function of wee1 causes a modest advancement of mitosis, whereas loss of both wee1 and mik1 function causes grossly premature mitosis, uncoupled from all checkpoints that normally restrain cell division (Lundgren et al. (1991) Cell 64:1111–1122).

As the cell is about to reach the end of G2, dephosphorylation of the cdc2-inactivating Thr-14 and Tyr-15 residues occurs leading to activation of the cdc2 complex as a kinase. A stimulatory phosphatase, known as cdc25, is responsible for Tyr-15 and Thr-14 dephosphorylation and serves as a rate-limiting mitotic activator. (Dunphy et al. (1991) Cell 67:189–196; Lee et al. (1992) Mol Biol Cell 3:73–84; Millar et al. (1991) EMBO J 10:4301–4309; and Russell et al. (1986) Cell 45:145–153). Recent evidence indicates that both the cdc25 phosphatase and the cdc2-specific tyrosine kinases are detectably active during interphase, suggesting that there is an ongoing competition between these two activities prior to mitosis (Kumagai et al. (1992) *Cell* 70:139–151; Smythe et al. (1992) *Cell* 68:787–797; and Solomon et al. (1990) *Cell* 63:1013–1024. This situation implies that the initial decision to enter mitosis involves a modulation of the equilibrium of the phosphorylation state of cdc2 which is likely controlled by variation of the rate of tyrosine dephosphorylation of cdc2 and/or a decrease in the rate of its tyrosine phosphorylation. A variety of genetic and biochemical data appear to favor a decrease in cdc2-specific trosine kinase activity near the initiation of mitosis which can serve as a triggering step to tip the balance in favor of cdc2 dephosphorylation (Smythe et al. (1992) *Cell* 68:787–797; Matsumoto et al. (1991) *Cell* 66:347–360; Kumagai et al. (1992) *Cell* 70:139–151; Rowley et al. (1992) *Nature* 356:353–355; and Enoch et al. (1992) *Genes Dev.* 6:2035–2046). Moreover, recent data suggest at the activated cdc2 kinase is responsible for phosphorylating and activating cdc25. This event would provide a self-amplifying loop and trigger a rapid increase in the activity of the cdc25 protein, ensuring that the tyrosine dephosphorylation of cdc2 proceeds rapidly to completion (Hoffmann et al. (1993) *EMBO J.* 12:53).

SUMMARY OF THE INVENTION

The present invention makes available assays and reagents for identifying anti-proliferative agents, such as mitotic and meiotic inhibitors. The present assay provides a simple and rapid screening test which relies on scoring for positive cellular proliferation as indicative of anti-mitotic or anti-meiotic activity, and comprises contacting a candidate agent with a cell which has an impaired cell-cycle checkpoint and measuring the level of proliferation in the presence and absence of the agent. The checkpoint impairment is such that it either causes premature progression of the cell through at least a portion of a cell-cycle or inhibition of normal progression of the cell through at least a portion of a cell-cycle, but can be off-set by the action of an agent which inhibits at least one regulatory protein of the cell-cycle in a manner which counter-balances the effect of the impairment. In one embodiment of the assay, anti-mitotic agents can be identified through their ability to rescue an otherwise hyper-mitotic cell from mitotic catastrophe by inhibiting the activity of at least one regulatory protein of the cell-cycle which acts as a mitotic activator. In another embodiment of the assay, an anti-mitotic agent can be identified by its ability to induce mitosis in an otherwise hypo-mitotic cell by inhibiting the activity of at least one regulatory protein of the cell-cycle which acts as a negative regulator of mitosis. In yet another embodiment of the invention, anti-meiotic agents can be identified by their ability to bring about faithful meiosis of an otherwise hyper-meiotic or hypo-meiotic cell.

The impaired checkpoint can be generated, for example, by molecular biological, genetic, and/or biochemical means. The checkpoint to be impaired can comprise a regulatory protein or proteins which control progression through the cell-cycle, such as those which control the G2/M transition or the G1/S transition. By way of example, the impaired checkpoint can comprise regulatory proteins which control the phosphorylation/dephosphorylation of a cdc protein kinase, such as the gene products of wee1, mik1, or nimi1.

The cell used in the assay (reagent cell) can be generated so as to favor scoring for anti-proliferative agents which specifically inhibit a particular cell-cycle activity. For example, if it is desirable to produce an inhibitor to a cdc25 phosphatase activity, a hyper-mitotic or hyper-meiotic cell can be generated which would be rescued from mitotic or meiotic catastrophe by partial inhibition of cdc25.

Furthermore, the hyper- and hypo-proliferative cells of the present assay, whether for identifying anti-mitotic or anti-meiotic agents, can be generated so as to comprise heterologous cell-cycle proteins (i.e. cross-species expression). For example, a cdc25 homolog from one species can be expressed in the cells of another species where it has been shown to be able to rescue loss-of-function mutations in that host cell. For example, a hyper-mitotic Schizosaccharomyces cell, such as *Schizosaccharomyces pombe*, can be constructed so as to comprise an exogenous cdc25 phosphatase and a conditionally impairable wee1 protein kinase. The exogenous cdc25 can be, for example, a human cdc25 homolog, or alternatively, a cdc25 homolog from a human pathogen.

DETAILED DESCRIPTION OF THE INVENTION

Figure 1:
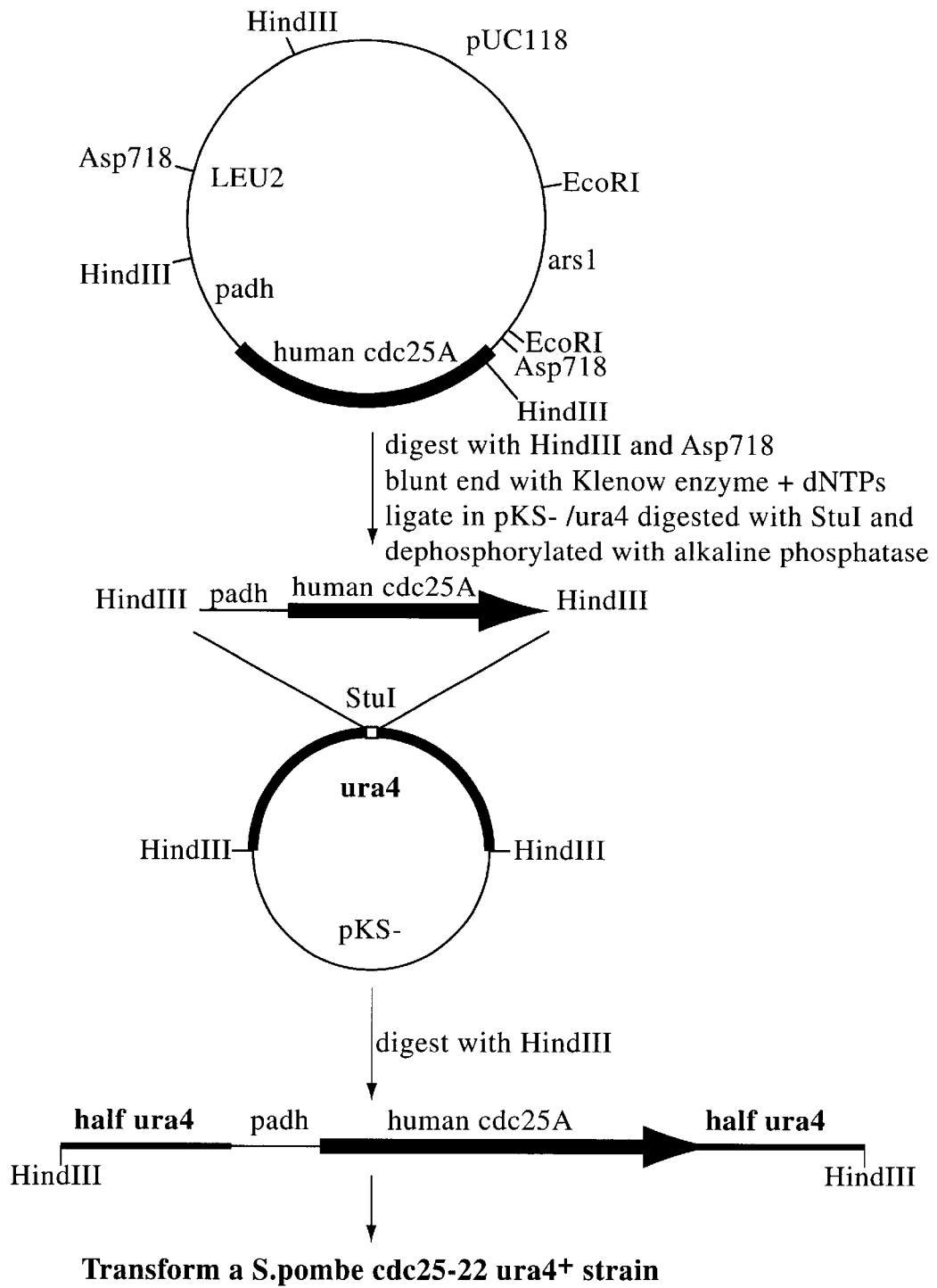
FIG. 1 is a schematic representation of the construction of the "5'-half ura4-adh promoter-cdc25A-3'-half ura4" nucleic acid fragment of Example 1 for transforming ura4+ *S. pombe* cells.

In dividing eukaryotic cells, circuits of regulatory proteins oversee both the initiation and completion of the major transitions of both the meiotic and mitotic cell-cycles. These regulatory networks guarantee that the successive events of each cell-cycle occur in a faithful and punctual manner. For example, mitosis cannot begin until the cell has grown sufficiently and replicated its genome accurately. Likewise, cell division cannot ensue until the mitotic spindle has distributed the chromosomes equally to both daughter cells.

The present invention makes available assays and reagents for identifying anti-mitotic and anti-meiotic agents. As described herein, anti-mitotic agents can be identified, in one embodiment of the present assay, through their ability to rescue an otherwise hyper-mitotic cell from mitotic catastrophe by inhibiting the activity of at least one regulatory protein of the cell-cycle which acts as a mitotic activator. The term hyper-mitotic cell denotes a cell having an impaired cell-cycle checkpoint which can cause premature progression of the cell though at least a portion of the cell-cycle and thereby results in inhibition of proliferation of the cell. The impaired checkpoint of the hyper-mitotic cell would otherwise act as a negative regulator of downstream mitotic events. Impairment of such a negative regulator consequently allows the cell to proceed aberrantly toward subsequent mitotic stages and ultimately inhibits faithful proliferation of the cell. In the presence of an agent able to inhibit a mitotic activator, progression of the hyper-mitotic cell through the cell-cycle can be slowed to enable the cell to appropriately undergo mitosis and proliferate with fidelity. In general, it will be expected that in order to detect an anti-mitotic agent in the present assay using a hyper-mitotic cell, the agent must inhibit a mitotic activator whose operation in the cell-cycle is sufficiently connected to the impaired checkpoint that the cell is prevented by the anti-mitotic agent from committing to the otherwise catastrophic events of prematurely passing the checkpoint. It is clear that an anti-mitotic agent effective at rescuing the hyper-mitotic cell in the present assay can do so by acting directly on the mitotic activator such as, for example, a phosphatase inhibitor might be expected to do to a cdc25 homolog. Alternatively, the anti-mitotic agent may exert its effect by preventing the activation of the mitotic activator, as, for example, inhibiting the phosphorylation step which activates cdc25 as a phosphatase, or inhibiting the activity of the cdc2 kinase with regard to other potential protein substrates.

In another embodiment of the present assay, an anti-mitotic agent can be identified by its ability to induce mitosis in an otherwise hypo-mitotic cell by inhibiting the activity of at least one regulatory protein of the cell-cycle which acts as a negative regulator of mitosis. The term hypo-mitotic cell refers to a cell which has an impaired checkpoint comprising an overly-active negative mitotic regulator which represses progression of the cell through at least a portion of the cell-cycle. In the presence of an agent able to inhibit the activity of the negative regulator, inhibition of the cell-cycle is overcome and the cell can proliferate at an increased rate relative to the untreated hypo-mitotic cell. As with the hyper-mitotic system above, it will generally be expected that an anti-mitotic agent detected in the hypo-mitotic system acts at, or sufficiently close to, the overly-active negative regulator so as to reduce its inhibitory effect on the cell-cycle.

In yet another embodiment of the present invention, anti-meiotic agents can be identified in a manner analogous to the anti-mitotic assay above, wherein faithful meiosis of either a hyper-meiotic or hypo-meiotic cell is measured in the presence and absence of a candidate agent. As above, the terms hyper-meiotic and hypo-meiotic refer to impaired meiotic checkpoints which are respectively of either diminished activity or enhanced activity relative to the normal meiotic cell.

The present assay provides a simple and rapid screening test which relies on scoring for positive proliferation as indicative of anti-mitotic activity. One advantage of the present assay is that while direct inhibition of growth can be caused by any toxic compound added to a proliferating cell culture, growth stimulation in the present assay will only be achieved upon specific inhibition of a mitotic activator where the assay comprises a hyper-mitotic cell, or upon inhibition of a negative mitotic regulator where the assay comprises a hypo-mitotic cell. In an analogous manner, positive meiotic progression can be utilized in the present assay as indicative of anti-meiotic activity of the candidate agent.

Other advantages of the present assays include the ability to screen for anti-mitotic and anti-meiotic activity in vivo, as well as the amenity of the assay to high through-put analysis. Anti-mitotic agents identified in the present assay can have important medical consequences and may be further tested for use in treating proliferative diseases which include a wide range of cancers, neoplasias, and hyperplasias, as well as for general or specific immunosuppression, such as through inhibition of the proliferation of lymphocytes. In addition, the present assay can be used to identify both anti-mitotic and anti-meiotic agents which can be used in the treatment of pathogenic infections such as fungal infections which give rise to mycosis. Anti-mitotic and anti-meiotic agents identified in the present assay may also be used, for example, in birth control methods by disrupting oogenic pathways in order to prevent the development of either the egg or sperm, or by preventing mitotic progression of a fertilized egg.

With regard to the hyper-mitotic cell and hypo-mitotic cell of the present assay, impairment of the negative regulatory checkpoint can be generated so as to be either continual or conditional. A conditional impairment permits the checkpoint to be normatively operational under some conditions such that the cell may proliferate and be maintained by cell culture techniques; and be rendered inoperative, or alternatively hyper-operative, under other conditions. In the instance of the hyper-mitotic cell, the impaired checkpoint is effectively inoperative to an extent that the impairment allows aberrant mitosis to occur which concludes in mitotic catastrophe. Conversely, the hypo-mitotic cell can be generated by an impaired checkpoint which is effectively hyper-operative and results in inhibition of the cell-cycle. A continual impairment, on the other hand, is one that is ever-present and which allows proliferation of the cell under conditions where there is no need to halt the cell at that checkpoint; but, in the instance of the hyper-mitotic cell, results in mitotic catastrophe under conditions where the cell-cycle must be halted, such as in the presence of DNA synthesis inhibitors or DNA damaging agents.

The impaired checkpoint can be generated, for example, by molecular biological, genetic, and/or biochemical means. The checkpoint to be impaired can comprise a regulatory protein or proteins which control progression through the cell-cycle, such as those which control the G2/M transition or the G1/S transition. Extensive genetic and biochemical analysis of these pathways (see, for example, *Molecular Biology of the Fission Yeast,* eds Nasi et al., Academic Press, San Diego, 1989) has led to the ability to manipulate the control of mitosis through loss-of-function and gain-of-function mutations and by plasmid overexpression, as well as by exposure of the cell to certain chemicals. The checkpoint impairment can be, for example, the result of directly altering the effective activity of a regulatory protein at the checkpoint (i.e. by altering its catalytic activity and/or concentration), or indirectly the result of modifying the action of another protein which is upstream of the checkpoint but which modulates the action of regulatory proteins at the checkpoint. For instance, various mutants have been isolated which are able to escape specific cell-cycle control circuits and progress inappropriately to the next cell-cycle stage and can be used to generate the hyper-mitotic cell. In a similar manner, mutants have been isolated which are unable to pass a specific cell-cycle checkpoint and are prevented from progressing to the next cell-cycle stage, and provide the basis for the hypo-mitotic cell of the present assay.

Genetic studies in eukaryotic systems, including mammalian and fungi, have identified several genes that are important for the proper timing of mitosis. For instance, in the fission yeast *S. pombe,* genes encoding regulators of cell division have been extensively characterized (for review see MacNeil et al. (1989) *Curr. Genet.* 16:1). As set out above, initiation of mitosis in fission yeast correlates with activation of the cdc2 protein kinase. cdc2 is a component of M phase promoting factor (MPF) purified from frogs and starfish, and homologs of cdc2 have been identified in a wide range of eukaryotes, suggesting that cdc2 plays a central role in mitotic control in all eukaryotic cells (Norbury et al. (1989) *Biochem. Biophys. Acta* 989:85). For purposes of the present disclosure, the term "cdc2" or "cdc protein kinase" is used synonymously with the recently adopted "cell division kinase" (cdk) nomenclature. Furthermore as used herein, the term cdc2 is understood to denote members of the cell division kinase family. Representative examples of cdc protein kinases include cdc2-SP, cdc28 (*S. cerevisiae*), cdk2-XL, cdc2-HS and cdk2-HS, where "HS" designates homosapiens, SP designates *S. pombe,* and "XL" designates *Xenopus laevis.* As set out above, the switch that controls the transition between the inactive cdc2/cyclin B complex (phosphorylated on Try-15 and Thr-14) present during S-G2-prophase and the active form of the cdc2/cyclin B kinase (dephosphorylated on Try-15 and Thr-14) present at metaphase is believed to correspond to a change in the relative activities of the opposing kinases and phosphatase (s) that act on the sites. Given that many regulatory pathways appear to converge on cdc protein kinases, as well as their activating role at both G1/S and G2/M transitions, the hyper-mitotic cell of the present assay can be employed to develop inhibitors specific for particular cdc protein kinases.

Regulatory pathways which feed into and modulate the activity of a cdc protein kinase can be manipulated to generate either the hyper-mitotic or hypo-mitotic cell of the present assay. For example, the inhibitory phosphorylation of cdc2 is mediated by at least two tyrosine kinases, initially identified in fission yeast and known as wee1 and mik1 (Russell et al. (1987) *Cell* 49:559; Lundgren et al. (1991) *Cell* 64:111; Featherstone et al. (1991) *Nature* 349:808; and Parker et al. (1991) *EMBO* 10:1255). These kinases act as mitotic inhibitors, overexpression of which causes cells to arrest in the G2 phase of the cell-cycle. For instance, overexpression of wee1 has been shown to cause intense phosphorylation of cdc2 (cdc28 in budding yeast) which results in cell-cycle arrest. Conversely, loss of function of wee1 causes advancement of mitosis and cells enter mitosis at approximately half the normal size, whereas loss of wee1 and mik1 function causes grossly premature initiation of mitosis, uncoupled from all checkpoints that normally restrain cell division. Thus, wee1 and mik1 each represent suitable regulatory proteins which could be impaired to generate either the hyper-mitotic or hypo-mitotic cell of the present assay.

Furthermore, it is apparent that enzymes which modulate the activity of the wee1 or mik1 kinases can also be pivotal in controlling the precise timing of mitosis. For example, the level of the nim1/cdr1 protein, a negative regulator of the wee1 protein kinase, can have a pronounced impact on the rate of mitotic initiation, and nim1 mutants have been shown to be defective in responding to nutritional deprivation (Russel et al. (1987) *Cell* 49:569; and Feilotter et al. (1991) *Genetics* 127:309). Over-expression of nim1 (such as the *S. pombe* op-nim1 mutant) can result in inhibition of the wee1 kinase and allow premature progression into mitosis. Loss of nim1 function, on the other hand, delays mitosis until the cells have grown to a larger size. In like manner, mutation in the stf1 gene has also been shown to relieve regulation of mitotic progression in response to DNA synthesis inhibition.

Loss-of-function strains, such as wee1-50, mik1::ura, or stf1-1 Rowley et al. (1992) *Nature* 356:353), are well known. In addition, each of the wee1, mik1, and nim1 genes have been cloned (see for example Coleman et al. (1993) *Cell* 72:919; and Feilotter et al. (1991) *Genetics* 127:309), such that disruption of wee1 and/or mik1 expression or over-expression of nim1 can be carried out to create the hyper-mitotic cell of the present assay. In a similar fashion, over-expression of wee1 and/or mik1 or disruption of nim1 expression can be utilized to generate the hypo-mitotic cell of the present assay. Furthermore, each of these negative mitotic regulators can also be a potential target for an anti-mitotic agent scored for using the hypo-mitotic cell of the present assay.

Acting antagonistically to the wee1/mik1 kinases, genetic and biochemical studies have indicated that the cdc25 protein is a central player in the process of cdc2-specific dephosphorylation and crucial to the activation of the cdc2 kinase activity. In the absence of cdc25, cdc2 accumulates in a tyrosine phosphorylated state and can cause inhibition of mitosis. The phosphatase activity of cdc25 performs as a mitotic activator and is therefore a suitable target for inhibition by an anti-mitotic agent in the present assay. It is strongly believed that this aspect of the mitotic control network is generally conserved among eukaryotes, though the particular mode of regulation of cdc25 activity may vary somewhat from species to species. Homologs of the fission yeast cdc25 have been identified in the budding yeast *S. cerevisiae* (Millar et al. (1991) *CSH Symp. Quant. Biol.* 56:577), humans (Galaktinov et al. (1990) *Cell* 67:1181; and Sadhu et al. (1989) *PNAS* 87:5139), mouse (Kakizuka et al. (1992) *Genes Dev.* 6:578), Drosophila (Edgar et al. (1989) *Cell* 57:177; and Glover (1991) *Trends Genet.* 7:125), and Xenopus (Kumagai et al., (1992) *Cell* 70:139; and Jessus et al. (1992) *Cell* 68:323). Human cdc25 is encoded by a multi-gene family now consisting of at least three members, namely cdc25A, cdc25B and cdc25C. As described below, all three homologs are able to rescue temperature-sensitive mutations of the *S. pombe* cdc25. Early evidence suggests that these different homologs may have different functions. For instance, microinjection of anti-cdc25-C antibodies into mammalian cells prevents them from dividing. They appear to arrest in interphase with a flattened morphology, consistent with a role for cdc25C in the entry into mitosis. On the contrary, microinjection of antibodies to cdc25A results in a rounded-up mitotic-like state, suggesting that the different homologs may have distinct functions and represent an additional level of complexity to the control of M-phase onset by cdc25 in higher eukaryotes. Comparison of the human cdc25's with each other and with cdc25 homologs from other species has been carried out. Comparison of cdc25A with cdc25C demonstrates a 48% identity in the 273aa C-terminal region between the two proteins; and comparison between cdc25B and cdc2SC reveals a 43% identify. The Drosophila cdc25 homolog "string" shares 34.5% identity to cdc25A in a 362 amino acid region and 43.9% in an 269 amino acid region with cdc25B. *S. pombe* cdc25 is also related to the human cdc25's, but to a lesser extent. Interestingly, the overall similarity between different human cdc25 proteins does not greatly exceed that between humans and such evolutionary distinct species as Drosophila. Biochemical experiments have demonstrated that bacterially produced cdc25 protein from Drosophila and human activates the histone H1 kinase activity of cdc2 in Xenopus or starfish extracts (Kumagai et al. (1991) *Cell* 64:903; and Strausfield et al. (1991) *Nature* 351:242).

If the cdc25 phosphatase activity is the desired target for development of an anti-mitotic agent, it may be advantageous to chose the hyper-mitotic cell of the present assay so as to more particularly select for anti-mitotic agents which act directly or indirectly on cdc25. As set out above, it will generally be expected that in order to score for an anti-mitotic agent in an assay relying on a hyper-mitotic cell, the inhibited mitotic activator (e.g. cdc25) must be sufficiently connected to the abherent checkpoint so as to rescue the cell before it concludes in mitotic catastrophe. Furthermore, the hyper-mitotic cell of the present assay can be generated by manipulation of the cell in which a cdc25 homolog is endogenously expressed, as for example, by generating a wee1 mutation (a "wee" phenotype), or by exposure of the cell to 2-aminopurine or caffeine after a γ-radiation induced G2 arrest. Alternatively, the cdc25 gene from one species or cell type can be cloned and subsequently expressed in a cell to which it is not endogenous but in which it is known to rescue lack-of-function mutations of the endogenous cdc25 activity. For example, the exogenous cdc25, such as a human cdc25, could be expressed in an hyper-mitotic Schizosaccharomyces cell, such as an *S. pombe* cell like the temperature-sensitive wee1-50 mutant. It may be possible to take advantage of the structural and functional differences between the human cdc25 phosphatases to provide anti-mitotic agents which selectively inhibit particular human cell types. In a similar manner, it may be feasible to develop cdc25 phosphatase inhibitors with the present assay which act specifically on pathogens, such as fungus involved in mycotic infections, without substantially inhibiting the human homologs.

The cdc2 activating kinase (CAK) represents yet another potential target for inhibition by an anti-mitotic agent which could be scored for using the hyper-mitotic cell of the present assay. Recent evidence indicates that many, if not all, of the cdc protein kinases require cyclin binding as well as phosphorylation at Thr-161 (Thr-161 of cdc2-HS; Thr-167 of cdc-2SP; Thr-169 of cdc28; and Thr-160 of cdk2-HS) for activation in vivo. CAK is believed to direct phosphorylation of Thr-161 in a cyclin-dependent manner and to act as a mitotic activator. Inhibition of CAK by a candidate agent may offset the effect of a hyper-mitotic checkpoint impairment which would otherwise have led to premature activation of a cdc protein kinase (e.g. as a wee1 deficient mutant would). In addition, CAK itself represents a possible site of impairment to generate the hyper-mitotic cell of the present assay. Overexpression of CAK can lead to premature activation of a cdc protein kinase and cause the cell to conclude in mitotic catastrophe.

Other checkpoints which could be impaired to generate the hyper-mitotic and hypo-mitotic systems have been identified by examination of mitotic events in cells treated in a manner which disrupts DNA synthesis or DNA repair. Radiation-induced arrest is one example of a checkpoint mechanism which has been used to identify both negative and positive regulators of mitosis. In this instance, mitosis is delayed until the integrity of the genome is checked and, as far as possible, restored. Checkpoint controls also function to delay mitosis until DNA synthesis is complete. The observation of cell-cycle arrest points indicate that the regulation of progression into mitosis in response to both DNA damage and the DNA synthesis requires components of the mitotic control. For example, analysis of radiation-sensitive mutations in budding yeast have identified a number of defective regulatory proteins which can prevent the arrest of the cell-cycle in response to DNA damage and are therefore potential candidates for impairment to generate the hyper-mitotic or hypo-mitotic cell of the present assay. By way of illustration, a number of genes involved in this mitotic feedback control have been identified, and include the rad9, rad17, rad24, mec1, mec2 and mec3 genes (Weinert et al. (1988) *Science* 241:317). All six genes have been shown to be negative regulators of cell-cycle progression and act in response to damaged DNA. Two genes, mec1 and mec2, are also involved in arresting the cell-cycle in response to unreplicated DNA.

The response to DNA damage has also been investigated in the fission yeast *S. pombe*. Mutations in a number of genes have been identified which allow cells with damaged or unreplicated DNA to enter mitosis. For example, the HUS12 and HUS16 genes have been implicated as negative regulators of mitosis which respond to unreplicated DNA, while RAD21 is a negative regulator sensitive to damaged DNA. The HUS14, HUS17, HUS22, HUS26, RAD1, RAD3, RAD9 and RAD17 genes of *S. pombe* each appear to be negative regulators of mitosis which are able to respond to either unreplicated or damaged DNA. (Rowley et al. (1992) *EMBO* 11:1343; and Enoch et al (1991) *CSH Symp. Quant. Biol.* 56:409)

Recently, mutations in the *S. cerevisiae* genes BUB and MAD have been isolated which fail to arrest in mitosis with microtubule-destabilizing drugs. (Hayt et al. (1491) *Cell* 66:507; and Li et al. (1991) *Cell* 66:519). The *S. cerevisiae* cell can also be affected by a number of environmental cues. One such effector is the α-mating factor which induces G1 arrest. Mutants in the FUS3 or FAR1 genes fail to arrest in G1 in response to α-factor. While mutations in either gene are phenotypically similar, they affect different regulatory pathways. For example, the FUS3 gene has been cloned and exhibits strong sequence similarity to the serine/threonine family of protein kinases (Goebl et al. (1991) *Curr. Opin. Cell Biol.* 3:242).

In the fungus *Aspergillus nidulans*, the bimE gene is believed to code for a negative regulator of mitosis that normally functions to prevent mitosis by controlling expression of a putative mitotic inducer, nimA. The absence of bimE function is believed to override cell-cycle control systems normally operative to prevent chromosome condensation and spindle formation from occurring during interphase. Temperature sensitive mutants of the bimE gene, such as the bimE7 mutant, allow cells with unreplicated DNA to prematurely enter mitosis (Osmani et al. (1988) *Cell* 52:241) and can be lethal phenotypes useful as hyper-mitotic cells of the present assay.

Checkpoints, and mutations thereof, have been identified in mammalian cells as well, and can be used to generate the hyper-mitotic and hypo-mitotic cells of the present assay. For instance, uncoupling of mitosis from completion of DNA replication has been reported in mammalian cells in response to drug treatment and mutation. In mammalian cells, as in other eukaryotic cells, DNA damage caused by mild X-ray irradiation can block passage through two cell-cycle checkpoints, the restriction point (G1/S) and entry into mitosis (G2/M) (Little et al. (1968) *Nature* 218:1064; Nagasawa et al. (1984) *Radiation Res.* 97:537; and Murray (1992) *Nature* 359:599). The AT gene(s), p53 and GADD45 are among genes which have been identified as critical to negative regulation of mitosis by cell-cycle checkpoints (Kaastan et al. (1992) *Cell* 71:587; Hartwell (1992) *Cell*

71:543; and Murray (1992) *Nature* 359:599) and can be utilized in the present assay to generate a hyper-mitotic cell or a hypo-mitotic cell depending on whether the impairment is brought about by disruption of expression, inhibition of activity, or by overexpression. Additionally, a temperature-sensitive mutation in the mammalian RCC1 (repressor of chromosome condensation) gene can cause cultured hamster cells to cease DNA replication and enter mitosis prematurely when they are shifted up to the nonpermissive temperature during S. phase. Relatives of RCC1 have also been identified in yeast (i.e. pim1) and Drosophila, and both genes can complement the mammalian RCC1 mutation, further suggesting that certain checkpoint mechanisms, like cdc2 regulation of the cell-cycle, are conserved across diverse phyla.

Many of the regulatory proteins involved in the progression of a cell through meiosis have also been identified. Because of the commonalty of certain mitotic and meiotic pathways, several mitotic regulatory proteins or their homologs, such as cdc protein kinases, cyclins, and cdc25 homologs, also serve to regulate meiosis. For example, cell division cycle mutants defective in certain mitotic cell-cycle events have been tested for sporulation at semi-restrictive temperatures (Gralbert et al. (1991) *Curr Genet* 20:199). The mitotic defective mutants cdc10-129, cdc20-M10, cdc21-M6B, cdc23-M36 and cdc24-M38 formed four-spored asci but with low efficiency. Mutants defective in the mitotic initiation genes cdc2, cdc25 and cdc13 were blocked at meiosis II, though none of the wee1-50, ddh. nim1+ and win1+ alleles had any affect on sporulation, suggesting that their interactions with cdc25 and cdc2 are specific to mitosis in yeast. Other regulatory genes and gene products which can be manipulated to form the hyper- or hypo-meiotic cells of the present invention include rec102, spo13, cut1, cut2, IME1, MAT, RME1, cdc35, BCY1, TPK1, TPY2, TPK3, spd1, spd3, spd4, spo50, spo51, and spo53. As above, the hyper- or hypo-meiotic cells can be generated genetically or chemically using cells to which the intended target of the anti-meiotic agent is endogenous, or alternatively, using cells in which the intended target is exogenously expressed.

In addition, certain meiotic regulatory proteins are able to rescue loss-of-function mutations in the mitotic cell-cycle. For example, the Drosophila meiotic cdc25 homolog, "twine", is able to rescue mitosis in temperature-sensitive cdc25 mutants of fission yeast. Thus, anti-meiotic agents can be identified using hyper- or hypo-meiotic cells, and in some instances, hyper- or hypo-mitotic cells.

It is also deemed to be within the scope of this invention that the hyper- and hypo-proliferative cells of the present assay, whether for identifying anti-mitotic or anti-meiotic agents, can be generated so as to comprise heterologous cell-cycle proteins (i.e. cross-species expression). As exemplified above in the instance of cdc25, cell-cycle proteins from one species can be expressed in the cells of another and have been shown to be able to rescue loss-of-function mutations in the host cell. In addition to those cell-cycle proteins which are ideally to be the target of inhibition by the candidate agent, cell-cycle proteins which interact with the intended inhibitor target can also be expressed across species. For example, in an hyper-proliferative yeast cell in which a human cdc25 (e.g. exogenously expressed) is the intended target for development of an anti-mitotic agent, a human cdc protein kinase and human cyclin can also be expressed in the yeast cell. Likewise, when a hypo-proliferative yeast expressing human wee1 is used, a human cdc protein kinase and human cyclin with which the human cdc25 would interact can be used to replace the corresponding yeast cell-cycle proteins. To illustrate, a triple cln deletion mutant of *S. cerevisae* which is also conditionally deficient in cdc28 (the budding yeast equivalent of cdc2) can be rescued by the co-expression of a human cyclin and human cdc2 proteins, demonstrating that yeast cell-cycle machinery can be at least in part replaced with corresponding human regulatory proteins. Roberts et al. (1993) PCT Publication Number WO 93106123. In this manner, the reagent cells of the present assay can be generated to more closely approximate the natural interactions which a particular cell-cycle protein might experience.

Manipulation of these regulatory pathways with certain drugs, termed here "hyper-mitotic agents", can induce mitotic aberrations and result in generation of the hyper-mitotic cell of the present assay. For instance, caffeine, the protein kinase inhibitors 2-aminopurine and 6-dimethylaminopurine, and the protein phosphatase inhibitor okadaic acid can cause cells that are arrested in S phase by DNA synthesis inhibitors to inappropriately enter mitosis (Schlegel et al. (1986) *Science* 232:1264; Schlegel et al. (1987) *PNAS* 84:9025; and Schlegel et al. (1990) *Cell Growth Differ.* 1:171). Further, 2-aminopurine is believed to be able to override a number of cell-cycle checkpoints from G1, S phase, G2, or mitosis. (Andreassen et al. (1992) *PNAS* 89:2272; Andreassen et al. (1991) *J. Cell Sci.* 100:299, and Steimnann et al. (1991) *PNAS* 88:6843). For example, 2-aminopurine permits cells to overcome a G2/M block induced by γ-irradiation. Additionally, cells continuously exposed to 2-aminopurine alone are able to exit S phase without completion of replication, and exit mitosis without metaphase, anaphase, or telophase events.

In an analogous manner, hypo-mitotic agents, such as a phosphatase inhibitor, can be utilized to chemically induce impairment of one or more regulatory pathways to produce the hypo-mitotic cell of the present assay. Likewise, hyper-meiotic or hypo-meiotic agents can be employed to chemically generate the appropriate reagent cell for identifying anti-meiotic agents in the present assay.

To aid in the facilitation of mitotic catastrophe in the hyper-mitotic cell it may be desirable to expose the cell to an agent (i.e. a chemical or environmental stimulus) which ordinarily induces cell-cycle arrest at that checkpoint. Inappropriate exit from the chemically- or environmentally-induced arrested state due to the impairment of the negative regulatory checkpoint can ultimately be lethal to the cell. Such arresting agents can include exposure to DNA damaging radiation or DNA damaging agents; inhibition of DNA synthesis and repair using DNA polymerase inhibitors such as hydroxyurea or aphidicolin; topoisomerase inhibitors such as 4'-dimethly-epipodophyllotoxin (VM-26); or agents which interfere with microtubule-assembly, such as Nocadazole and taxol. By way of example, BHK and HeLa cells which receive 250 rads of γ radiation have been shown to undergo G2 arrest that was reversed without further treatment within 4–5 hours. However, in the presence of either caffeine, 2-aminopurine, or 6-dimethyl-aminopurine, this mitotic delay was suppressed in both the hamster and human cells, and allowed the cells undergo mitosis before DNA repair had been completed (Steinmann et al. (1991) *PNAS* 88:6843). Additionally, in certain cells, nutritional status of the cell, as well as mating factors, can cause arrest of the normal cell during mitosis.

The present assay can be used to develop inhibitors of fungal infections. The most common fungal infections are superficial and are presently treated with one of several topical drugs or with the oral drugs ketoconazole or griseofulvin. The systemic mycoses constitute quite a different therapeutic problem. These infections are often very difficult to treat and long-term, parenteral therapy with potentially toxic drugs may be required. The systemic mycoses are sometimes considered in two groups according to the infecting organism. The "opportunistic infections" refer to those mycoses—candidiasis, aspergillosis, cryptococcosis, and phycomycosis— that commonly occur in debilitated and immunosuppressed patients. These infections are a particular problem in patients with leukemias and lymphomas, in people who are receiving immunosuppressive therapy, and in patients with such predisposing factors as diabetes mellitus or AIDS. Other systemic mycoses—for example, blastomycosis, histoplasmosis, coccidiodomycosis, and sporotrichosis— tend to have a relatively low incidence that may vary considerably according to geographical area.

To develop an assay for anti-mitotic or anti-meiotic agents having potential therapeutic value in the treatment of a certain mycotic infection, a yeast implicated in the infection can be used to generate the appropriate reagent cell of the present assay. For example, the hyper-mitotic or hypo-mitotic cell can be generated biochemically as described above, or engineered, as for example, by screening for radiation-sensitive mutants having impaired checkpoints. Additionally, a putative mitotic regulator of the mycotic yeast, such as a cdc25 homolog, can be cloned and expressed in a heterologous cell which may be easier to manipulate or facilitate easier measurement of proliferation, such as member of the Schizosaccharomyces genus like *S. pombe.*

By way of illustration, the present assays can be used to screen for anti-mitotic and anti-meiotic agents able to inhibit at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise either a hyper-mitotic or hypo-mitotic cells generated directly from, or with genes cloned from, yeast selected from the group consisting of *Candida albicans, Candida stellatoidea, Candida tropicalis, Candida parapsilosis, Candida krusei, Candida pseudotropicalis, Candida quillermondii,* and *Candida rugosa.* Likewise, the present assay can be used to identify anti-mitotic and anti-meiotic agents which may have therapeutic value in the treatment of aspergillosis by making use of yeast such as *Aspergillus fumigatus, Aspergillus flavus, Aspergillus niger, Aspergillus nidulans,* or *Aspergillus terreus.* Where the mycotic infection is mucormycosis, the yeast can be selected from a group consisting of *Rhizopus arrhizus, Rhizopus oryzae, Absidia corymbifera, Absidia ramosa,* and *Mucor pusillus.* Another pathogen which can be utilized in the present assay is *Pneumocystis carinii.*

Agents to be tested for their ability to act as anti-mitotic and/or anti-meiotic agents in the present assay can be those produced by bacteria, yeast or other organisms, or those produced chemically. The assay can be carried out in any vessel suitable for the growth of the cell, such as microtitre plates or petri dishes. As potent inhibitors mitosis and/or meiosis can fully inhibit proliferation of a cell, it may be useful to perform the assay at various concentrations of the candidate agent. For example, serial dilutions of the candidate agents can be added to the hyper-mitotic cell such that at at least one concentration tested the anti-mitotic agent inhibits the mitotic activator to an extent necessary to adequately slow the progression of the cell through the cell-cycle but not to the extent necessary to inhibit entry into mitosis all together. In a like manner, where the assay comprises a hypo-mitotic cell, serial dilutions of a candidate agent can be added to the cells such that, at at least one concentration, an anti-mitotic agent inhibits a negative mitotic regulator to an extent necessary to adequately enhance progression of the cell through the cell-cycle, but not to an extent which would cause mitotic catastrophe.

Quantification of proliferation of the hyper-mitotic cell in the presence and absence of a candidate agent can be measured with a number of techniques well known in the art, including simple measurement of population growth curves. For instance, where the assay involves proliferation in a liquid medium, turbidimetric techniques (i.e. absorbence/transmittance of light of a given wavelength through the sample) can be utilized. For example, in the instance where the reagent cell is a yeast cell, measurement of absorbence of light at a wavelength between 540 and 600 nm can provide a conveniently fast measure of cell growth.

Likewise, ability to form colonies in solid medium (e.g. agar) can be used to readily score for proliferation. Both of these techniques, especially with respect to yeast cells, are suitable for high through-put analysis necessary for rapid screening of large numbers of candidate agents. In addition, the use of solid media such as agar can further aid in establishing a serial dilution of the candidate agent. For example, the candidate agent can be spotted on a lawn of reagent cells plated on a solid media. The diffusion of the candidate agent through the solid medium surrounding the site at which it was spotted will create a diffusional effect. For anti-mitotic or anti-meiotic agents scored for in the present assay, a halo of cell growth would be expected in an area which corresponds to concentrations of the agent which offset the effect of the impaired checkpoint, but which are not so great as to over-compensate for the impairment or too little so as to be unable to rescue the cell.

To further illustrate, other proliferative scoring techniques useful in the present assay include measuring the mitotic index for untreated and treated cells; uptake of detectable nucleotides, amino acids or dyes; as well as visual inspection of morphological details of the cell, such as chromatin structure or other features which would be distinguishable between cells advancing appropriately through mitosis and cells concluding in mitotic catastrophe or stuck at certain cell-cycle checkpoint. In the instance of scoring for meiosis, morphology of the spores or gametes can be assessed. Alternatively, the ability to form a viable spore of gamete can be scored as, for example, measuring the ability of a spore to re-enter negative growth when contacted with an appropriate fermentable media.

To test compounds that might specifically inhibit the human cdc25A, cdc25B or cdc25C gene products, the genes were introduced into the genome of an *S. pombe* strain which was engineered to be conditionally hyper-mitotic. Three linear DNA fragments were constructed, each carrying one of the three human cdc25A, B or C genes under the control of an *S. pombe* promoter, and flanked by nucleic acid sequences which allow integration of the DNA into the *S. pombe* genome. The cdc25-containing DNA fragments are then used to transform an appropriate *S. pombe* strain. For example, in one embodiment, the expression of the human cdc25 gene is driven by the strong adh promoter and the flanking sequences of the fragment contain the ura4gene to allow integration of the fragment at the ura4locus by homologous recombination (Grimm et al. (1988) *Molec. gen. Genet* 81–86). The *S. pombe* strain is a wee1 temperature-sensitive mutant which becomes hyper-mitotic at temperatures above 36° C., and carries a wild-type ura4gene in which the cdc25 DNA fragment can be integrated.

Example 1

The human cdc25A gene has been previously cloned (see Galaktinov et al. (1991) *Cell* 67:1181). The sequence of the cdc25A gene containing the open reading frame is shown in Seq. ID No. 1, and is predicted to encode a protein of 523 amino acids (Seq. ID No. 2). A 2.0 kb NcoI-KpnI fragment encoding amino acids 1–523 of human cdc25A was subcloned into a NcoI-KpnI-(partially) digested pARTN expression vector, resulting in the pARTN-cdc25A construct harboring human cdc25A cDNA in sense orientation to the constitutive adh promoter. The *S. pombe* autonomously replicating pARTN vector is derived from pART3 (McLeod et al. (1987) *EMBO* 6:729) by ligation of a NcoI linker (New England Biolabs) into the SmaI site.

A 2.3 kb DNA fragment corresponding to the adh promoter and amino acids 1–523 of the human cdc25A gene, was isolated by digesting the pARTN-cdc25A plasmid with HindIII and Asp718. While HindIII is sufficient to isolate the adh promoter/human cdc25A gene fragment from the plasmid, we also used Asp718 to cut the close migrating 2.2 kb HindIII-HindIII *S. cerevisiae* LEU2 gene in two smaller fragments which makes isolation of the cdc25A fragment easier.

The HindIII/HindIII fragment was then blunt ended with Klenow enzyme and dNTPs (see *Molecular Cloning: A Laboratory Manual* 2ed, eds. Sambrook et al., CSH Laboratory Press: 1989) and ligated into a pKS-/ura4plasmid previously digested with StuI and dephosphorylated with alkaline phosphatase. Massive amounts of the recombinant plasmid were prepared, and a 4.1 kb DNA fragment corresponding to "5'-half ura4-adh promoter-cdc25A-3'-half ura4" (see FIG. 1) was isolated.

Example 2

The human cdc25B gene has been previously cloned (see Galaktinov et al. (1991) *Cell* 67:1181). The sequence of the cdc25B gene containing the open reading frame is shown in Seq. ID. No. 3, and is predicted to encode a protein of 566 amino acids (Seq. ID No. 4). A 2.4 kb SmaI fragment from the p4x1.2 plasmid (Galaktinov et al., supra) encoding amino acids 32–566 was subcloned into a SmaI-digested pART3 vector, resulting in the pARTN-cdc25B vector containing the human cdc25B cDNA. While the site of initiation of translation is not clear (there is no exogenous ATG 5' to the SmaI cloning site in the cdc25B open reading frame) we speculate that the first ATG corresponds to the Met-59 of the human cdc25B open reading frame, or alternatively, an ATG at an NdeI site of pART3. In any event, the pARTN-cdc25B plasmid has been shown to be capable of transforming *S. pombe* cells and able to rescue temperature-sensitive mutations of the yeast cdc25 gene (Galaktinov et al., supra).

Figure 2:
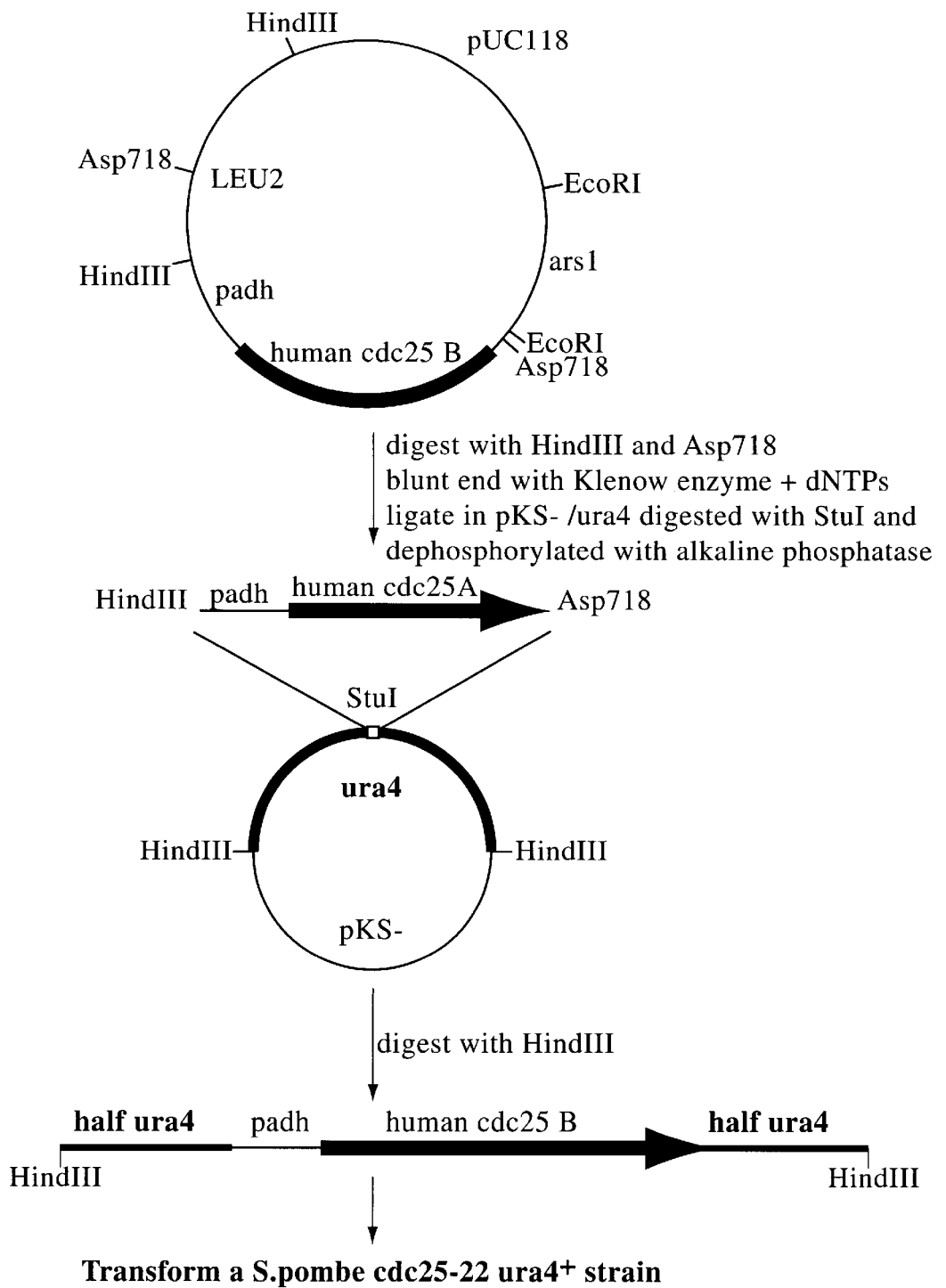
FIG. 2 is a schematic representation of the construction of the "5'-half ura4-adh promoter-cdc25B-3'-half ura4" nucleic acid fragment of Example 2 for transforming ura4+ *S. pombe* cells.

As above, a 2.7 kb DNA fragment, corresponding to the adh promoter and amino acids 32–566 of the human cdc25B gene, was isolated by digesting pARTN-cdc25B with HindIII and Asp718. The HindIII/HindIII cdc25B fragment was blunt ended with Klenow enzyme and dNTPs, and ligated into a pKS-/ura4vector previously digested with StuI and dephosphorylated with alkaline phosphatase. A 4.4 kb DNA fragment corresponding to "5'-half ura4-adh promoter-cdc-25B-3'-half ura4" (see FIG. 2) was isolated.

Example 3

Figure 3:
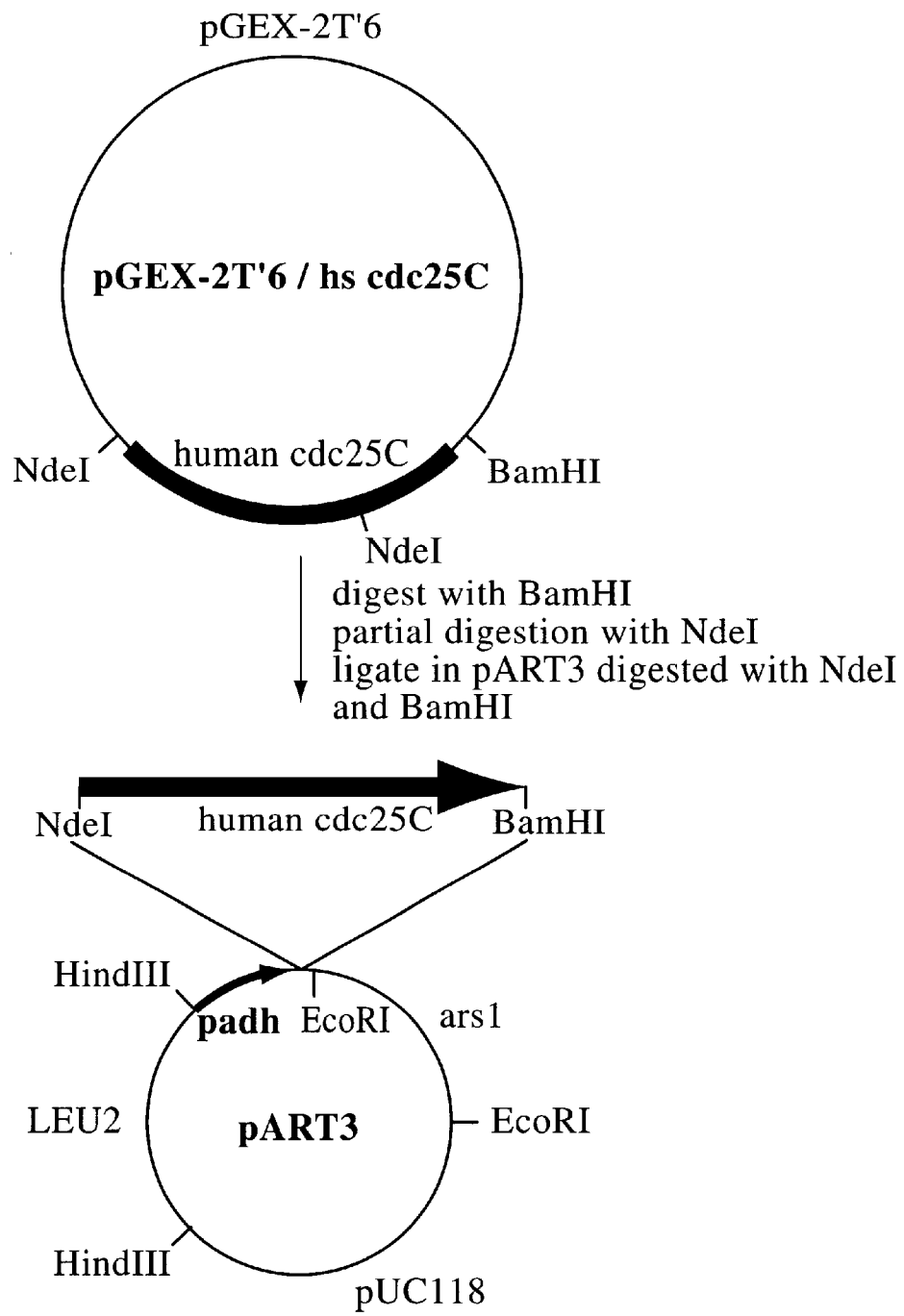
FIG. 3 is a schematic representation of the construction of the pART3-cdc25C plasmid of Example 3.

The human cdc25C gene has been previously cloned (see Sadhu et al. (1990) *PNAS* 87:115139; and Hoffmann et al. (1993) *EMBO* 12:53). The sequence of the cdc25C gene containing the open reading frame is shown in Seq. ID No. 5, and is predicted to encode a protein of 473 amino acids (Seq. ID No. 6). Beginning with the pGEX-2T6-cdc25 plasmid (Hoffmann et al., supra) a 1.8 kbp DNA fragment corresponding to amino acids 1–473 of the human cdc25C gene was isolated digestion with BamHI and by partial digestion with NdeI (i.e., there is a NdeI site in the cdc25C gene). This fragment was ligated into a pART3 vector previously digested with NdeI and BamHI, resulting in the plasmid pART3-cdc25C which contained the amino acids 1–473 of the human cdc25C gene under the control of the strong adh promoter (see FIG. 3).

Figure 4:
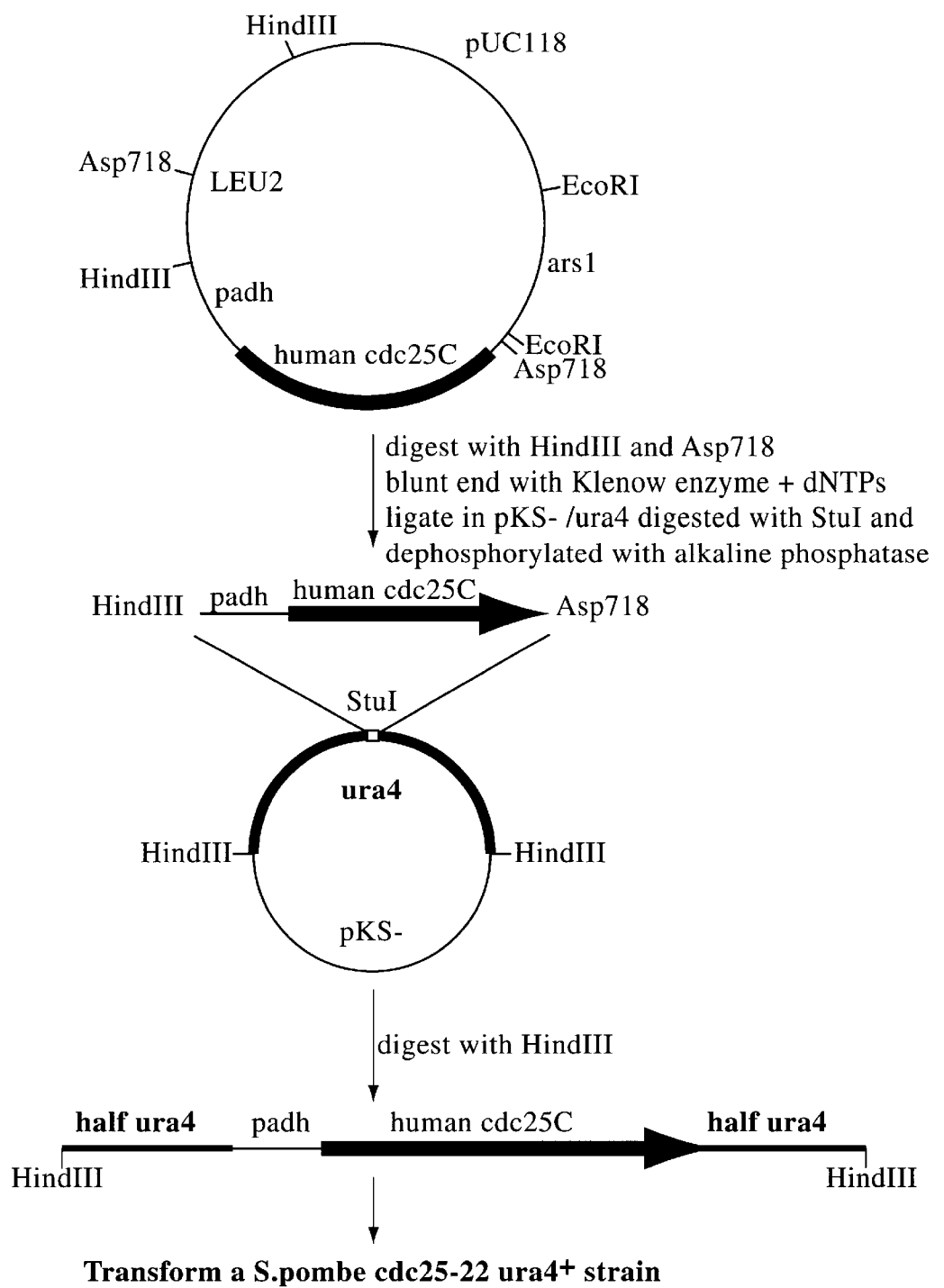
FIG. 4 is a schematic representation of the construction of the "5'-half ura4-adh promoter-cdc25C-3'-half ura4" nucleic acid fragment of Example 3 for transforming ura4+ *S. pombe* cells.

A 2.5 kbp fragment corresponding to the adh promoter and amino acids 1–473 of the human cdc25C gene was isolated by digesting pART3-cdc25C with HindIII and Asp718. The HindIII/HindIII cdc25C fragment was blunt ended with Klenow enzyme and dNTPs, and ligated into a pKS-/ura4plasmid previously digested with StuI and dephosphorylated with alkaline phosphatase. A 4.3 kbp DNA fragment corresponding to "5'-half ura4-adh promoter-cdc25C-3'-half ura4" (see FIG. 4) was isolated.

Example 4

Each of the cdc25 plasmid constructs pARTN-cdc25A, pARTN-cdc25B, and pART3-cdc25C, as well as the original pART3 plasmid, were used to transform the *S. pombe* strain Sp553 (h+N, cdc25-22, wee1-50, leuI-32) using well known procedures. Briefly, cells were grown in YE medium at 25° C. until they were in exponential phase (~$10^7$ cells/ml). The cells were then spun down from the media at 3000 rpm for 5 minutes, and resuspended in LiCl/TE at a concentration of ~$10^8$ cells/ml (LiCl/TE=10 mM Tris, 1 mM EDTA, 50 mM LiCl, Ph 8). The resuspended cells were incubated at room temperature for 10 minutes, then spun again at 3000 rpm for 5 minutes, resuspended in LiCl/TE to a concentration of ~$5 \times 10^8$ cells/ml, and shaken for 30 minutes at 25° C.

To an aliquot of 150 μl of cells, 500 ng of plasmid DNA and 350 μL of PEG/TE (10 mM Tris, 1 mM EDTA, 50% PEG 4000, Ph 8) was added. The cell/plasmid mixture was then incubated for 30 minutes at 25° C., heat shocked at 42° C. for 20 minutes, then spun at 15,000 rpm for 10 seconds after the addition of 0.5 mL of Edinburgh Minimal Medium (EMM). The cells were resuspended in 0.6 mL EMM, and 0.2 mL aliquots were plated.

Figure 5A:
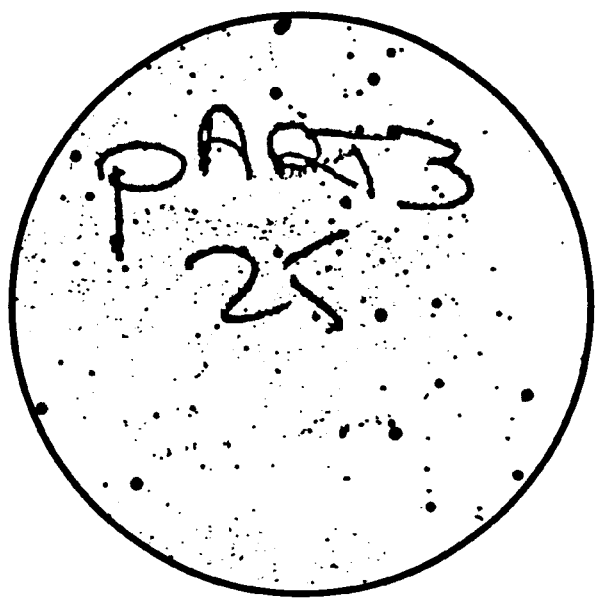
FIGS. 5A and 5B are photographs of yeast colonies formed by *S. pombe* cells transformed with pART3 plasmid, grown at 25° C. and 37° C. respectively.
Figure 5B:

FIGS. 5A and 5B illustrate the ability of the pART3 transformed yeast to grow at 25° C. and 37° C. respectively. As set out above, at the non-permissive temperature of 37° C., both the endogenous wee1 and cdc25 activities are impaired such that they mutually off-set each others effects, and the cells are still able to proliferate (pART3 lacks any cdc25 gene).

Figure 6A:
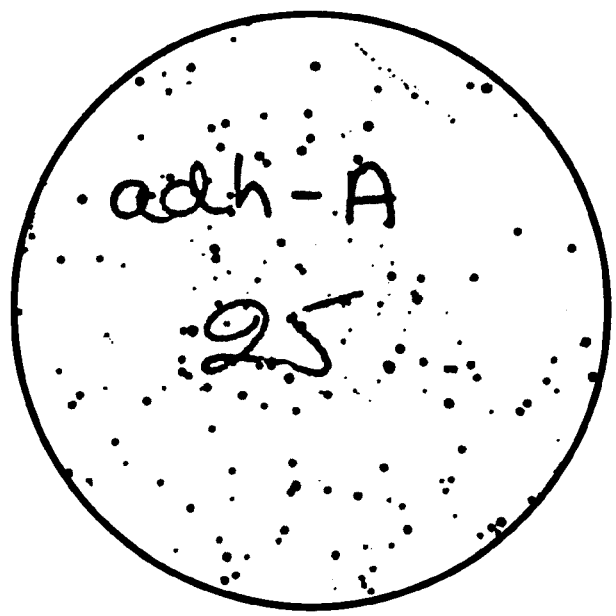
FIGS. 6A and 6B are photographs of yeast colonies formed by *S. pombe* cells transformed with the pARTN-cdc25A plasmid of Example 1, grown at 25° C. and 37° C. respectively.
Figure 6B:
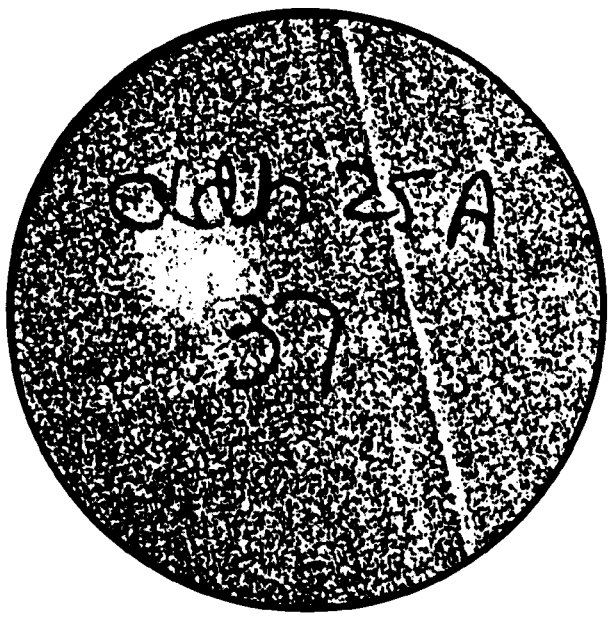
Figure 7A:
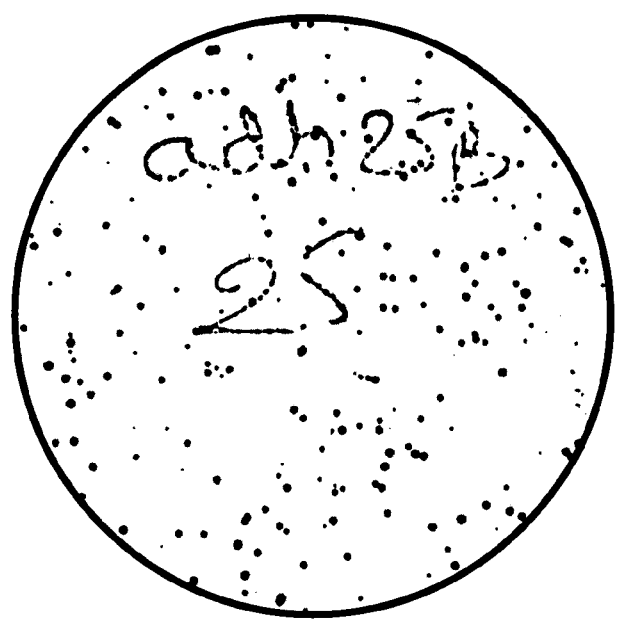
FIGS. 7A and 7B are photographs of yeast colonies formed by *S. pombe* cells transformed with the pARTN-cdc25B plasmid of Example 1, grown at 25° C. and 37° C. respectively.
Figure 7B:
Figure 8A:
FIGS. 8A and 8B are photographs of yeast colonies formed by *S. pombe* cells transformed with the pARTN-cdc25C plasmid of Example 1, grown at 25° C. and 37° C. respectively.
Figure 8B:
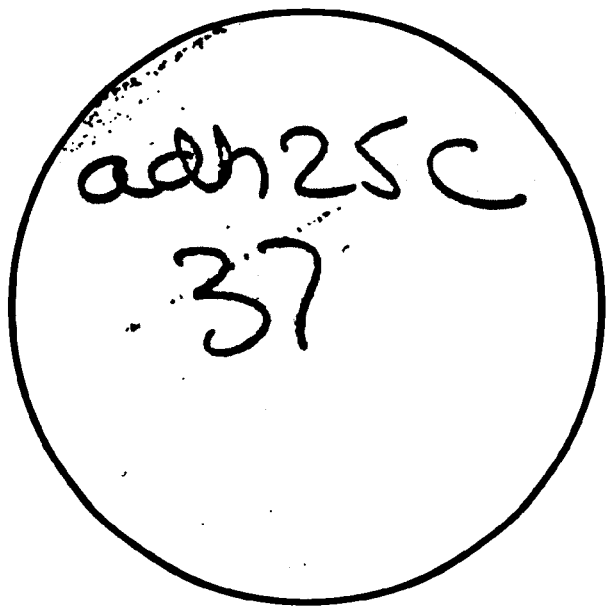

FIGS. 6A and 6B (cdc25A), 7A and 7B (cdc25B), and 8A and 8B (cdc25C) demonstrate the effect of expressing a human cdc25 in a yeast "wee" background. Each of FIGS. 6A, 7A and 8A show that at the permissive temperature of 25° C. (wee1 is expressed) the cells are able to proliferate. However, as illustrated by FIGS. 6B, 7B and 8B, shifting the temperature to the non-permissive temperature of 37° C. results in mitotic catastrophe. Microscopic analysis of the yeast cells present on the 37° C. plates revealed that the expression of a human cdc25 in a yeast wee background resulted in mitotic catastrophe for the cells.

Example 5

To provide a more stable transformant and uniform expression of the human cdc25 gene, each of the resulting ura4-cdc25 fragments of Examples 1–3 was used to transform a ura4+ *S. pombe* strain. As in Example 4, each of the *S. pombe* strain carried a thermosensitive allele of its own cdc25 gene, such as the cdc25-22 phenotype, so that at non-permissive temperatures the exogenous cdc25 is principally responsible for activation of cdc2. In one embodiment, the *S. pombe* wee1-50 cdc25-22 ura4+ strain was transformed with a ura4-cdc25 fragment of Examples 1–3. This particular strain is generally viable at 25° C. as well as the restrictive temperature of 37° C. as the loss of endogenous cdc25 activity is recovered by the concomitant loss of wee1 function at 37° C. However, integration and over expression of the human cdc25, as demonstrated in Example 4, can result in a mitotic catastrophic phenotype at 37° C. as the wee1 checkpoint is impaired.

Example 6

To assay the anti-mitotic activity of various candidate agents, the cells of Example 4 or 5 are either plated on a solid medium such as EMM plates or suspended in an appropriate vegetative broth such as YE.

In the instance of plating on a solid medium, candidate agents are subsequently blotted onto the plate, and the plate incubated at the non-permissive temperature of 37° C. A halo of cell growth will form surrounding those agents able to at least partially inhibit a mitotic activator which can rescue the otherwise catastrophic cell.

Where growth of the cells is carried out in a vegetative broth, aliquots of cell/media are placed in the wells of microtitre plates and serial dilutions of candidate agents are added to the wells. The plates are incubated at 37° C., and the $A_{540}$ for each well measured over time and compared to similar wells of cells/media which lack the candidate agent (e.g. negative controls). An increase in absorbence over time relative to the negative controls indicates positive proliferation of the cells and suggests an ability of a particular candidate agent to inhibit a mitotic activator.

All of the above-cited references and publications are hereby incorporated by reference.

Equivalents

Those skilled in the art will recognize, or be able to ascertain using no more than routine experimentation, numerous equivalents to the specific assay and reagents described herein. Such equivalents are considered to be within the scope of this invention and are covered by the following claims.

What is claimed:

1. An assay for identifying an anti-mitotic agent, comprising
   i. providing a culture of eukaryotic cells overexpressing a recombinant nucleic acid for a mammalian mitotic activator which activates a cyclin dependent kinase (CDK), wherein said mammalian mitotic activator is selected from the group consisting of mammalian cdc25 phosphatase and mammalian cdc2 activating kinase (CAK); and wherein said cells have an impaired cell-cycle checkpoint caused by decreased inhibitory phosphorylation of the CDK or increased activating phosphorylation of the CDK which causes premature entry of the cells into mitosis so as to cause cell death, the premature entry into mitosis being mediated at least in part by the activation of the CDK by the mitotic activator;
   ii. contacting the culture of cells with a candidate agent under conditions wherein the cell-cycle checkpoint is impaired;
   iii. measuring a level of proliferation of the cells in the presence of the candidate agent; and
   iv. comparing the level of proliferation of the cells in the presence of the candidate agent to a level of proliferation of the cells in the absence of the candidate agent, wherein an increase in the level of proliferation in the presence of the candidate agent is indicative of anti-mitotic activity of the candidate agent.

2. An assay for identifying an anti-mitotic agent, comprising
   i. providing a culture of eukaryotic cells having an impaired cell-cycle checkpoint caused at least in part by overexpression of a recombinant nucleic acid encoding a mammalian mitotic activator selected from the group consisting of mammalian cdc25 phosphatase and mammalian cdc2 activating kinase (CAK), wherein said mitotic activator activates a cyclin dependent kinase (CDK) thereby causing premature entry of the cells into mitosis so as to cause cell death;
   ii. contacting the culture of cells with a candidate agent under conditions wherein the cell-cycle checkpoint is impaired;
   iii. measuring a level of proliferation of the cells in the presence of the candidate agent; and
   iv. comparing the level of proliferation of the cells in the presence of the candidate agent to a level of proliferation of the cells in the absence of the candidate agent, wherein an increase in the level of proliferation in the presence of the candidate agent is indicative of anti-mitotic activity of the candidate agent.

3. An assay for identifying an anti-mitotic agent, comprising
   i. providing a culture of eukaryotic cells having an impaired cell-cycle checkpoint caused at least in part by overexpression of a recombinant nucleic acid encoding cdc2 activating kinase (CAK), wherein said CAK activates a cyclin-dependent kinase (CDK) thereby causing premature entry of the cells into mitosis so as to cause cell death;
   ii. contacting the culture of cells with a candidate agent under conditions wherein the cell-cycle checkpoint is impaired;

iii. measuring a level of proliferation of the cells in the presence of the candidate agent; and iv. comparing the level of proliferation of the cells in the presence of the candidate agent to a level of proliferation of the cells in the absence of the candidate agent, wherein an increase in the level of proliferation in the presence of the candidate agent is indicative of anti-mitotic activity of the candidate agent.

4. An assay for identifying an anti-mitotic agent, comprising i. providing a culture of eukaryotic cells overexpressing a recombinant nucleic acid for a mitotic activator which activates a cyclin dependent kinase (CDK), wherein said mitotic activator is selected from the group consisting of cdc25 phosphatase and cdc2 activating kinase (CAK); and wherein said cells have an impaired cell-cycle checkpoint caused by decreased inhibitory phosphorylation of the CDK or increased activating phosphorylation of the CDK which causes premature entry of the cells into mitosis so as to cause cell death, the premature entry into mitosis being mediated at least in part by the activation of the CDK by the mitotic activator, wherein the impaired cell-cycle checkpoint is induced by treatment of the cell with a hyper-mitotic agent;

ii. contacting the culture of cells with a candidate agent under conditions wherein the cell-cycle checkpoint is impaired;

iii. measuring a level of proliferation of the cells in the presence of the candidate agent; and iv. comparing the level of proliferation of the cells in the presence of the candidate agent to a level of proliferation of the cells in the absence of the candidate agent, wherein an increase in the level of proliferation in the presence of the candidate agent is indicative of anti-mitotic activity of the candidate agent.

5. An assay for identifying an anti-mitotic agent, comprising i. providing a culture of eukaryotic cells having an impaired G1/S cell-cycle checkpoint caused by either decreased inhibitory phosphorylation of a cyclin dependent kinase (CDK), or by increased activating phosphorylation of the CDK, which impaired checkpoint causes premature entry of the cells into mitosis so as to cause cell death, wherein said impaired checkpoint comprises impaired wee1 protein kinase activity, impaired mik1 protein kinase activity or over-expression of a nim1 gene product;

ii. contacting the culture of cells with a candidate agent under conditions wherein the cell-cycle checkpoint is impaired;

iii. measuring a level of proliferation of the cells in the presence of the candidate agent; and iv. comparing the level of proliferation of the cells in the presence of the candidate agent to a level of proliferation of the cells in the absence of the candidate agent, wherein an increase in the level of proliferation in the presence of the candidate agent is indicative of anti-mitotic activity of the candidate agent.

6. The assay of claim 1, wherein the cell-cycle checkpoint comprises a G1/S checkpoint.

7. The assay of claim 1, wherein the cell-cycle checkpoint comprises a G2/M checkpoint.

8. The assay of claim 2, wherein the cell-cycle checkpoint comprises a G1/S checkpoint.

9. The assay of claim 2, wherein the cell-cycle checkpoint comprises a G2/M checkpoint.

10. The assay of claim 2, wherein the cell-cycle checkpoint is conditionally impairable.

11. The assay of claim 1, wherein the impaired cell-cycle checkpoint results in entry of the cell into mitosis before completion of replication or repair of genomic DNA of the cell.

12. The assay of claim 1, wherein the impaired cell-cycle checkpoint comprises a reduction of inhibitory phosphorylation of a cyclin dependent kinase (cdk).

13. The assay of claim 12, wherein the impaired cell-cycle checkpoint comprises an impaired wee1 protein kinase activity, an impaired mik1 protein kinase activity, or an over-expression of a nim1 gene product.

14. The assay of claim 1, wherein the cell-cycle checkpoint is conditionally impairable.

15. The assay of claim 1, wherein the impaired cell-cycle checkpoint is induced by treatment of the cell with a hyper-mitotic agent.

16. The assay of claim 15, wherein the hyper-mitotic agent is selected from the group consisting of caffeine, 2-aminopurine, 6-dimethylaminopurine, and okadaic acid.

17. The assay of claim 1 or 2, wherein the mammalian mitotic activator is a mammalian cdc25 phosphatase.

18. The assay of claim 17, wherein the mammalian cdc25 phosphatase is a human cdc25 phosphatase.

19. The assay of claim 1 or 2, wherein the mitotic activator is a cdc2 activating kinase (CAK).

20. The assay of claim 1, wherein the eukaryotic cells are yeast cells.

21. The assay of claim 20, wherein the yeast cells comprise a species of the genus Schizosaccharomyces.

22. The assay of claim 1, wherein the eukaryotic cells are mammalian cells.

23. The assay of claim 2, wherein the eukaryotic cells are mammalian cells.

24. The assay of claim 22, wherein the mammalian cells are human cells.

25. The assay of claim 23, wherein the mammalian cells are human cells.

* * * * *

```
                          SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 2420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 460..2031

(xi) SEQUENCE DESCRIPTION: SEQ ID NO: 1:

CGAAAGGCCG GCCTTGGCTG CGACAGCCTG GGTAAGAGGT GTAGGTCGGC TTGGTTTTCT        60

GCTACCCGGA GCTGGGCAAG CGGGTGGGGA GAACAGCGAA GACAGCGTGA GCCTGGGCCG       120

TTGCCTCGAG GCTCTCGCCC GGCTTCTCTT GCCGACCCGC CACGTTTGTT TGGATTTAAT       180

CTTACAGCTG GTTGCCGGCG CCCGCCCGCC CGCTGGCCTC GCGGTGTGAG AGGGAAGCAC       240

CCGTGCCTGT GTCTCGTGGC TGGCGCCTGG AGGGTCCGCA CACCCGCGCG GCCGCGCCGC       300

TTTGCCCGCG GCAGCCGCGT CCCTGAACCG CGGAGTCGTG TTTGTGTTTG ACCCGCGGGC       360

GCCGGTGGCG CGCGGCCGAG GCCGGTGTCG GCGGGGCGGG GCGGTCGCGC GGGAGGCAGA       420

GGAAGAGGGA GCGGGAGCTC TGCGAGGCCG GGCGCCGCC ATG GAA CTG GGC CCG         474
                                             Met Glu Leu Gly Pro
                                              1               5

AGC CCC GCA CCG CGC CGC CTG CTC TTC GCC TGC AGC CCC CCT CCC GCG        522
Ser Pro Ala Pro Arg Arg Leu Leu Phe Ala Cys Ser Pro Pro Pro Ala
                10                  15                  20

TCG CAG CCC GTC GTG AAG GCG CTA TTT GGC GCT TCA GCC GCC GGG GGA        570
Ser Gln Pro Val Val Lys Ala Leu Phe Gly Ala Ser Ala Ala Gly Gly
            25                  30                  35

CTG TCG CCT GTC ACC AAC CTG ACC GTC ACT ATG GAC CAG CTG CAG GGT        618
Leu Ser Pro Val Thr Asn Leu Thr Val Thr Met Asp Gln Leu Gln Gly
```

-continued

```
                       40                          45                          50
CTG GGC AGT GAT TAT GAG CAA CCA CTG GAG GTG AAG AAC AAC AGT AAT         666
Leu Gly Ser Asp Tyr Glu Gln Pro Leu Glu Val Lys Asn Asn Ser Asn
         55                          60                          65

CTG CAG ATA ATG GGC TCC TCC AGA TCA ACA GAT TCA GGT TTC TGT CTA         714
Leu Gln Ile Met Gly Ser Ser Arg Ser Thr Asp Ser Gly Phe Cys Leu
 70                          75                          80                      85

GAT TCT CCT GGG CCA TTG GAC AGT AAA GAA AAC CTT GAA AAT CCT ATG         762
Asp Ser Pro Gly Pro Leu Asp Ser Lys Glu Asn Leu Glu Asn Pro Met
                     90                          95                         100

AGA AGA ATA CAT TCC CTA CCT CAA AAG CTG TTG GGA TGT AGT CCA GCT         810
Arg Arg Ile His Ser Leu Pro Gln Lys Leu Leu Gly Cys Ser Pro Ala
                 105                         110                         115

CTG AAG AGG AGC CAT TCT GAT TCT CTT GAC CAT GAC ATC TTT CAG CTC         858
Leu Lys Arg Ser His Ser Asp Ser Leu Asp His Asp Ile Phe Gln Leu
             120                         125                         130

ATC GAC CCA GAT GAG AAC AAG GAA AAT GAA GCC TTT GAG TTT AAG AAG         906
Ile Asp Pro Asp Glu Asn Lys Glu Asn Glu Ala Phe Glu Phe Lys Lys
         135                         140                         145

CCA GTA AGA CCT GTA TCT CGT GGC TGC CTG CAC TCT CAT GGA CTC CAG         954
Pro Val Arg Pro Val Ser Arg Gly Cys Leu His Ser His Gly Leu Gln
150                         155                         160                     165

GAG GGT AAA GAT CTC TTC ACA CAG AGG CAG AAC TCT GCC CAG CTC GGA         1002
Glu Gly Lys Asp Leu Phe Thr Gln Arg Gln Asn Ser Ala Gln Leu Gly
                 170                         175                         180

ATG CTT TCC TCA AAT GAA AGA GAT AGC AGT GAA CCA GGG AAT TTC ATT         1050
Met Leu Ser Ser Asn Glu Arg Asp Ser Ser Glu Pro Gly Asn Phe Ile
             185                         190                         195

CCT CTT TTT ACA CCC CAG TCA CCT GTG ACA GCC ACT TTG TCT GAT GAG         1098
Pro Leu Phe Thr Pro Gln Ser Pro Val Thr Ala Thr Leu Ser Asp Glu
         200                         205                         210

GAT GAT GGC TTC GTG GAC CTT CTC GAT GGA GAC AAT CTG AAG AAT GAG         1146
Asp Asp Gly Phe Val Asp Leu Leu Asp Gly Asp Asn Leu Lys Asn Glu
215                         220                         225

GAG GAG ACC CCC TCG TGC ATG GCA AGC CTC TGG ACA GCT CCT CTC GTC         1194
Glu Glu Thr Pro Ser Cys Met Ala Ser Leu Trp Thr Ala Pro Leu Val
230                         235                         240                     245

ATG AGA ACT ACA AAC CTT GAC AAC CGA TGC AAG CTG TTT GAC TCC CCT         1242
Met Arg Thr Thr Asn Leu Asp Asn Arg Cys Lys Leu Phe Asp Ser Pro
                 250                         255                         260

TCC CTG TGT AGC TCC AGC ACT CGG TCA GTG TTG AAG AGA CCA GAA CGT         1290
Ser Leu Cys Ser Ser Ser Thr Arg Ser Val Leu Lys Arg Pro Glu Arg
             265                         270                         275

TCT CAA GAG GAG TCT CCA CCT GGA AGT ACA AAG AGG AGG AAG AGC ATG         1338
Ser Gln Glu Glu Ser Pro Pro Gly Ser Thr Lys Arg Arg Lys Ser Met
         280                         285                         290

TCT GGG GCC AGC CCC AAA GAG TCA ACT AAT CCA GAG AAG GCC CAT GAG         1386
Ser Gly Ala Ser Pro Lys Glu Ser Thr Asn Pro Glu Lys Ala His Glu
     295                         300                         305

ACT CTT CAT CAG TCT TTA TCC CTG GCA TCT TCC CCC AAA GGA ACC ATT         1434
Thr Leu His Gln Ser Leu Ser Leu Ala Ser Ser Pro Lys Gly Thr Ile
310                         315                         320                     325

GAG AAC ATT TTG GAC AAT GAC CCA AGG GAC CTT ATA GGA GAC TTC TCC         1482
Glu Asn Ile Leu Asp Asn Asp Pro Arg Asp Leu Ile Gly Asp Phe Ser
                 330                         335                         340

AAG GGT TAT CTC TTT CAT ACA GTT GCT GGG AAA CAT CAG GAT TTA AAA         1530
Lys Gly Tyr Leu Phe His Thr Val Ala Gly Lys His Gln Asp Leu Lys
             345                         350                         355

TAC ATC TCT CCA GAA ATT ATG GCA TCT GTT TTG AAT GGC AAG TTT GCC         1578
```

```
                                                                    -continued Tyr Ile Ser Pro Glu Ile Met Ala Ser Val Leu Asn Gly Lys Phe Ala
            360                 365                 370

AAC CTC ATT AAA GAG TTT GTT ATC ATC GAC TGT CGA TAC CCA TAT GAA      1626
Asn Leu Ile Lys Glu Phe Val Ile Ile Asp Cys Arg Tyr Pro Tyr Glu
        375                 380                 385

TAC GAG GGA GGC CAC ATC AAG GGT GCA GTG AAC TTG CAC ATG GAA GAA      1674
Tyr Glu Gly Gly His Ile Lys Gly Ala Val Asn Leu His Met Glu Glu
390                 395                 400                 405

GAG GTT GAA GAC TTC TTA TTG AAG AAG CCC ATT GTA CCT ACT GAT GGC      1722
Glu Val Glu Asp Phe Leu Leu Lys Lys Pro Ile Val Pro Thr Asp Gly
                410                 415                 420

AAG CGT GTC ATT GTT GTG TTT CAC TGC GAG TTT TCT TCT GAG AGA GGT      1770
Lys Arg Val Ile Val Val Phe His Cys Glu Phe Ser Ser Glu Arg Gly
            425                 430                 435

CCC CGC ATG TGC CGG TAT GTG AGA GAG AGA GAT CGC CTG GGT AAT GAA      1818
Pro Arg Met Cys Arg Tyr Val Arg Glu Arg Asp Arg Leu Gly Asn Glu
        440                 445                 450

TAC CCC AAA CTC CAC TAC CCT GAG CTG TAT GTC CTG AAG GGG GGA TAC      1866
Tyr Pro Lys Leu His Tyr Pro Glu Leu Tyr Val Leu Lys Gly Gly Tyr
455                 460                 465

AAG GAG TTC TTT ATG AAA TGC CAG TCT TAC TGT GAG CCC CCT AGC TAC      1914
Lys Glu Phe Phe Met Lys Cys Gln Ser Tyr Cys Glu Pro Pro Ser Tyr
470                 475                 480                 485

CGG CCC ATG CAC CAC GAG GAC TTT AAA GAA GAC CTG AAG AAG TTC CGC      1962
Arg Pro Met His His Glu Asp Phe Lys Glu Asp Leu Lys Lys Phe Arg
                490                 495                 500

ACC AAG AGC CGG ACC TGG GCA GGG GAG AAG AGC AAG AGG GAG ATC TAC      2010
Thr Lys Ser Arg Thr Trp Ala Gly Glu Lys Ser Lys Arg Glu Ile Tyr
            505                 510                 515

AGT CGT CTG AAG AAG CTC TGAGGGCGGC AGGACCAGCC AGCAGCAGCC             2058
Ser Arg Leu Lys Lys Leu
            520

CAAGCTTCCC TCCATCCCCC TTTACCCTCT TTCCTGCAGA GAAACTTAAG CAAAGGGGAC    2118

AGCTGTGTGA CATTTGGAGA GGGGGCCTGG GACTTCCATG CCTTAAACCT ACCTCCCACA    2178

CTCCCAAGGT TGGAGACCCA GGCCATCTTG CTGGCTACGC CTCTTCTGTC CCTGTTAGAC    2238

GTCCTCCGTC CATTACAGAA CTGTGCCACA ATGCAGTTCT GAGCACCGTG TCAAGCTGCT    2298

CTGAGCCACA GTGGGATGAA CCAGCCGGGG CCTTATCGGG CTCCAGCATC TCATGAGGGG    2358

AGAGGAGACG GAGGGGACTA GAGAAGTTTA CACAGAAATG CTGCTGGCCA AATAGCAAAG    2418

AG                                                                  2420

(2) INFORMATION FOR SEQ ID NO: 2:

(i) SEQUENCE CHARACTERISTICS:
        (A) LENGTH: 523 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Leu Gly Pro Ser Pro Ala Pro Arg Arg Leu Leu Phe Ala Cys
1               5                   10                  15

Ser Pro Pro Ala Ser Gln Pro Val Val Lys Ala Leu Phe Gly Ala
            20                  25                  30

Ser Ala Ala Gly Gly Leu Ser Pro Val Thr Asn Leu Thr Val Thr Met
        35                  40                  45

Asp Gln Leu Gln Gly Leu Gly Ser Asp Tyr Glu Gln Pro Leu Glu Val
```

-continued

```
                50                      55                      60
Lys Asn Asn Ser Asn Leu Gln Ile Met Gly Ser Ser Arg Ser Thr Asp
 65                      70                      75                      80

Ser Gly Phe Cys Leu Asp Ser Pro Gly Pro Leu Asp Ser Lys Glu Asn
                         85                      90                      95

Leu Glu Asn Pro Met Arg Arg Ile His Ser Leu Pro Gln Lys Leu Leu
                        100                     105                     110

Gly Cys Ser Pro Ala Leu Lys Arg Ser His Ser Asp Ser Leu Asp His
                        115                     120                     125

Asp Ile Phe Gln Leu Ile Asp Pro Asp Glu Asn Lys Glu Asn Glu Ala
                130                     135                     140

Phe Glu Phe Lys Lys Pro Val Arg Pro Val Ser Arg Gly Cys Leu His
145                     150                     155                     160

Ser His Gly Leu Gln Glu Gly Lys Asp Leu Phe Thr Gln Arg Gln Asn
                        165                     170                     175

Ser Ala Gln Leu Gly Met Leu Ser Ser Asn Glu Arg Asp Ser Ser Glu
                        180                     185                     190

Pro Gly Asn Phe Ile Pro Leu Phe Thr Pro Gln Ser Pro Val Thr Ala
                        195                     200                     205

Thr Leu Ser Asp Glu Asp Asp Gly Phe Val Asp Leu Leu Asp Gly Asp
210                     215                     220

Asn Leu Lys Asn Glu Glu Thr Pro Ser Cys Met Ala Ser Leu Trp
225                     230                     235                     240

Thr Ala Pro Leu Val Met Arg Thr Thr Asn Leu Asp Asn Arg Cys Lys
                        245                     250                     255

Leu Phe Asp Ser Pro Ser Leu Cys Ser Ser Thr Arg Ser Val Leu
                        260                     265                     270

Lys Arg Pro Glu Arg Ser Gln Glu Glu Ser Pro Pro Gly Ser Thr Lys
                        275                     280                     285

Arg Arg Lys Ser Met Ser Gly Ala Ser Pro Lys Glu Ser Thr Asn Pro
290                     295                     300

Glu Lys Ala His Glu Thr Leu His Gln Ser Leu Ser Leu Ala Ser Ser
305                     310                     315                     320

Pro Lys Gly Thr Ile Glu Asn Ile Leu Asp Asn Asp Pro Arg Asp Leu
                        325                     330                     335

Ile Gly Asp Phe Ser Lys Gly Tyr Leu Phe His Thr Val Ala Gly Lys
                        340                     345                     350

His Gln Asp Leu Lys Tyr Ile Ser Pro Glu Ile Met Ala Ser Val Leu
                        355                     360                     365

Asn Gly Lys Phe Ala Asn Leu Ile Lys Glu Phe Val Ile Asp Cys
370                     375                     380

Arg Tyr Pro Tyr Glu Tyr Glu Gly Gly His Ile Lys Gly Ala Val Asn
385                     390                     395                     400

Leu His Met Glu Glu Glu Val Glu Asp Phe Leu Leu Lys Lys Pro Ile
                        405                     410                     415

Val Pro Thr Asp Gly Lys Arg Val Ile Val Phe His Cys Glu Phe
                        420                     425                     430

Ser Ser Glu Arg Gly Pro Arg Met Cys Arg Tyr Val Arg Glu Arg Asp
                        435                     440                     445

Arg Leu Gly Asn Glu Tyr Pro Lys Leu His Tyr Pro Glu Leu Tyr Val
                        450                     455                     460

Leu Lys Gly Gly Tyr Lys Glu Phe Phe Met Lys Cys Gln Ser Tyr Cys
465                     470                     475                     480
```

```
Glu Pro Pro Ser Tyr Arg Pro Met His His Glu Asp Phe Lys Glu Asp
                485                 490                 495
Leu Lys Lys Phe Arg Thr Lys Ser Arg Thr Trp Ala Gly Lys Ser
            500                 505                 510
Lys Arg Glu Ile Tyr Ser Arg Leu Lys Lys Leu
        515                 520

(2) INFORMATION FOR SEQ ID NO: 3:

(i) SEQUENCE CHARACTERISTICS:
        (A) LENGTH: 2886 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 73..1773

(xi) SEQUENCE DESCRIPTION: SEQ ID NO: 3:

CTGCCCTGCG CCCCGCCCTC CAGCCAGCCT GCCAGCTGTG CCGGCGTTTG TTGGTCTGCC      60

GGCCCCGCCG CG ATG GAG GTG CCC CAG CCG GAG CCC GCG CCA GGC TCG         108
              Met Glu Val Pro Gln Pro Glu Pro Ala Pro Gly Ser
                1               5                  10

GCT CTC AGT CCA GCA GGC GTG TGC GGT GGC GCC CAG CGT CCG GGC CAC       156
Ala Leu Ser Pro Ala Gly Val Cys Gly Gly Ala Gln Arg Pro Gly His
            15                  20                  25

CTC CCG GGC CTC CTG CTG GGA TCT CAT GGC CTC CTG GGG TCC CCG GTG       204
Leu Pro Gly Leu Leu Leu Gly Ser His Gly Leu Leu Gly Ser Pro Val
    30                  35                  40

CGG GCG GCC GCT TCC TCG CCG GTC ACC ACC CTC ACC CAG ACC ATG CAC       252
Arg Ala Ala Ala Ser Ser Pro Val Thr Thr Leu Thr Gln Thr Met His
 45                 50                  55                  60

GAC CTC GCC GGG CTC GGC AGC CGC AGC CGC CTG ACG CAC CTA TCC CTG       300
Asp Leu Ala Gly Leu Gly Ser Arg Ser Arg Leu Thr His Leu Ser Leu
                65                  70                  75

TCT CGA CGG GCA TCC GAA TCC TCC CTG TCG TCT GAA TCC TCC GAA TCT       348
Ser Arg Arg Ala Ser Glu Ser Ser Leu Ser Ser Glu Ser Ser Glu Ser
            80                  85                  90

TCT GAT GCA GCT CTC TGC ATG GAT TCC CCC AGC CCT CTG GAC CCC CAC       396
Ser Asp Ala Ala Leu Cys Met Asp Ser Pro Ser Pro Leu Asp Pro His
        95                  100                 105

ATG GCG GAG CAG ACG TTT GAA CAG GCC ATC CAG GCA GCC AGC CGG ATC       444
Met Ala Glu Gln Thr Phe Glu Gln Ala Ile Gln Ala Ala Ser Arg Ile
    110                 115                 120

ATT CGA AAC GAG CAG TTT GCC ATC AGA CGC TTC CAG TCT ATG CCG GTG       492
Ile Arg Asn Glu Gln Phe Ala Ile Arg Arg Phe Gln Ser Met Pro Val
125                 130                 135                 140

AGG CTG CTG GGC CAC AGC CCC GTG CTT CGG AAC ATC ACC AAC TCC CAG       540
Arg Leu Leu Gly His Ser Pro Val Leu Arg Asn Ile Thr Asn Ser Gln
                145                 150                 155

GCG CCC GAC GGC CGG AGG AAG AGC GAG GCG GGC AGT GGA GCT GCC AGC       588
Ala Pro Asp Gly Arg Arg Lys Ser Glu Ala Gly Ser Gly Ala Ala Ser
            160                 165                 170

AGC TCT GGG GAA GAC AAG GAG AAT GAT GGA TTT GTC TTC AAG ATG CCA       636
Ser Ser Gly Glu Asp Lys Glu Asn Asp Gly Phe Val Phe Lys Met Pro
        175                 180                 185

TGG AAC CCC ACA CAT CCC AGC TCC ACC CAT GCT CTG GCA GAG TGG GCC       684
Trp Asn Pro Thr His Pro Ser Ser Thr His Ala Leu Ala Glu Trp Ala
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 190 |     |     |     |     | 195 |     |     |     |     | 200 |     |      |
| AGC | CGC | AGG | GAA | GCC | TTT | GCC | CAG | AGA | CCC | AGC | TCG | GCC | CCC | GAC | CTG | 732  |
| Ser | Arg | Arg | Glu | Ala | Phe | Ala | Gln | Arg | Pro | Ser | Ser | Ala | Pro | Asp | Leu |      |
| 205 |     |     |     | 210 |     |     |     |     | 215 |     |     |     |     | 220 |     |      |
| ATG | TGT | CTC | AGT | CCT | GAC | CCG | AAG | ATG | GAA | TTG | GAG | GAG | CTC | AGC | CCC | 780  |
| Met | Cys | Leu | Ser | Pro | Asp | Pro | Lys | Met | Glu | Leu | Glu | Glu | Leu | Ser | Pro |      |
|     |     |     |     | 225 |     |     |     |     | 230 |     |     |     |     | 235 |     |      |
| CTG | GCC | CTA | GGT | CGC | TTC | TCT | CTG | ACC | CCT | GCA | GAG | GGG | GAT | ACT | GAG | 828  |
| Leu | Ala | Leu | Gly | Arg | Phe | Ser | Leu | Thr | Pro | Ala | Glu | Gly | Asp | Thr | Glu |      |
|     |     |     | 240 |     |     |     |     | 245 |     |     |     |     | 250 |     |     |      |
| GAA | GAT | GAT | GGA | TTT | GTG | GAC | ATC | CTA | GAG | AGT | GAC | TTA | AAG | GAT | GAT | 876  |
| Glu | Asp | Asp | Gly | Phe | Val | Asp | Ile | Leu | Glu | Ser | Asp | Leu | Lys | Asp | Asp |      |
|     |     | 255 |     |     |     |     | 260 |     |     |     |     | 265 |     |     |     |      |
| GAT | GCA | GTT | CCC | CCA | GGC | ATG | GAG | AGT | CTC | ATT | AGT | GCC | CCA | CTG | GTC | 924  |
| Asp | Ala | Val | Pro | Pro | Gly | Met | Glu | Ser | Leu | Ile | Ser | Ala | Pro | Leu | Val |      |
|     | 270 |     |     |     |     | 275 |     |     |     |     | 280 |     |     |     |     |      |
| AAG | ACC | TTG | GAA | AAG | GAA | GAG | GAA | AAG | GAC | CTC | GTC | ATG | TAC | AGC | AAG | 972  |
| Lys | Thr | Leu | Glu | Lys | Glu | Glu | Glu | Lys | Asp | Leu | Val | Met | Tyr | Ser | Lys |      |
| 285 |     |     |     |     | 290 |     |     |     |     | 295 |     |     |     |     | 300 |      |
| TGC | CAG | CGG | CTC | TTC | CGC | TCT | CCG | TCC | ATG | CCC | TGC | AGC | GTG | ATC | CGG | 1020 |
| Cys | Gln | Arg | Leu | Phe | Arg | Ser | Pro | Ser | Met | Pro | Cys | Ser | Val | Ile | Arg |      |
|     |     |     |     | 305 |     |     |     |     | 310 |     |     |     |     | 315 |     |      |
| CCC | ATC | CTC | AAG | AGG | CTG | GAG | CGG | CCC | CAG | GAC | AGG | GAC | ACG | CCC | GTG | 1068 |
| Pro | Ile | Leu | Lys | Arg | Leu | Glu | Arg | Pro | Gln | Asp | Arg | Asp | Thr | Pro | Val |      |
|     |     |     | 320 |     |     |     |     | 325 |     |     |     |     | 330 |     |     |      |
| CAG | AAT | AAG | CGG | AGG | CGG | AGC | GTG | ACC | CCT | CCT | GAG | GAG | CAG | CAG | GAG | 1116 |
| Gln | Asn | Lys | Arg | Arg | Arg | Ser | Val | Thr | Pro | Pro | Glu | Glu | Gln | Gln | Glu |      |
|     |     | 335 |     |     |     |     | 340 |     |     |     |     | 345 |     |     |     |      |
| GCT | GAG | GAA | CCT | AAA | GCC | CGC | GCT | CTC | CGC | TCA | AAA | TCA | CTG | TGT | CAC | 1164 |
| Ala | Glu | Glu | Pro | Lys | Ala | Arg | Ala | Leu | Arg | Ser | Lys | Ser | Leu | Cys | His |      |
| 350 |     |     |     |     | 355 |     |     |     |     | 360 |     |     |     |     |     |      |
| GAT | GAG | ATC | GAG | AAC | CTC | CTG | GAC | AGT | GAC | CAC | CGA | GAG | CTG | ATT | GGA | 1212 |
| Asp | Glu | Ile | Glu | Asn | Leu | Leu | Asp | Ser | Asp | His | Arg | Glu | Leu | Ile | Gly |      |
| 365 |     |     |     |     | 370 |     |     |     |     | 375 |     |     |     |     | 380 |      |
| GAT | TAC | TCT | AAG | GCC | TTC | CTC | CTA | CAG | ACA | GTA | GAC | GGA | AAG | CAC | CAA | 1260 |
| Asp | Tyr | Ser | Lys | Ala | Phe | Leu | Leu | Gln | Thr | Val | Asp | Gly | Lys | His | Gln |      |
|     |     |     |     | 385 |     |     |     |     | 390 |     |     |     |     | 395 |     |      |
| GAC | CTC | AAG | TAC | ATC | TCA | CCA | GAA | ACG | ATG | GTG | GCC | CTA | TTG | ACG | GGC | 1308 |
| Asp | Leu | Lys | Tyr | Ile | Ser | Pro | Glu | Thr | Met | Val | Ala | Leu | Leu | Thr | Gly |      |
|     |     |     | 400 |     |     |     |     | 405 |     |     |     |     | 410 |     |     |      |
| AAG | TTC | AGC | AAC | ATC | GTG | GAT | AAG | TTT | GTG | ATT | GTA | GAC | TGC | AGA | TAC | 1356 |
| Lys | Phe | Ser | Asn | Ile | Val | Asp | Lys | Phe | Val | Ile | Val | Asp | Cys | Arg | Tyr |      |
|     |     | 415 |     |     |     |     | 420 |     |     |     |     | 425 |     |     |     |      |
| CCC | TAT | GAA | TAT | GAA | GGC | GGG | CAC | ATC | AAG | ACT | GCG | GTG | AAC | TTG | CCC | 1404 |
| Pro | Tyr | Glu | Tyr | Glu | Gly | Gly | His | Ile | Lys | Thr | Ala | Val | Asn | Leu | Pro |      |
|     | 430 |     |     |     |     | 435 |     |     |     |     | 440 |     |     |     |     |      |
| CTG | GAA | CGC | GAC | GCC | GAG | AGC | TTC | CTA | CTG | AAG | AGC | CCC | ATC | GCG | CCC | 1452 |
| Leu | Glu | Arg | Asp | Ala | Glu | Ser | Phe | Leu | Leu | Lys | Ser | Pro | Ile | Ala | Pro |      |
| 445 |     |     |     |     | 450 |     |     |     |     | 455 |     |     |     |     | 460 |      |
| TGT | AGC | CTG | GAC | AAG | AGA | GTC | ATC | CTC | ATT | TTC | CAC | TGT | GAA | TTC | TCA | 1500 |
| Cys | Ser | Leu | Asp | Lys | Arg | Val | Ile | Leu | Ile | Phe | His | Cys | Glu | Phe | Ser |      |
|     |     |     | 465 |     |     |     |     | 470 |     |     |     |     | 475 |     |     |      |
| TCT | GAG | CGT | GGG | CCC | CGC | ATG | TGC | CGT | TTC | ATC | AGG | GAA | CGA | GAC | CGT | 1548 |
| Ser | Glu | Arg | Gly | Pro | Arg | Met | Cys | Arg | Phe | Ile | Arg | Glu | Arg | Asp | Arg |      |
|     |     | 480 |     |     |     |     | 485 |     |     |     |     | 490 |     |     |     |      |
| GCT | GTC | AAC | GAC | TAC | CCC | AGC | CTC | TAC | TAC | CCT | GAG | ATG | TAT | ATC | CTG | 1596 |
| Ala | Val | Asn | Asp | Tyr | Pro | Ser | Leu | Tyr | Tyr | Pro | Glu | Met | Tyr | Ile | Leu |      |
|     | 495 |     |     |     |     | 500 |     |     |     |     | 505 |     |     |     |     |      |
| AAA | GGC | GGC | TAC | AAG | GAG | TTC | TTC | CCT | CAG | CAC | CCG | AAC | TTC | TGT | GAA | 1644 |

```
Lys Gly Gly Tyr Lys Glu Phe Phe Pro Gln His Pro Asn Phe Cys Glu
    510                 515                 520

CCC CAG GAC TAC CGG CCC ATG AAC CAC GAG GCC TTC AAG GAT GAG CTA    1692
Pro Gln Asp Tyr Arg Pro Met Asn His Glu Ala Phe Lys Asp Glu Leu
525                 530                 535                 540

AAG ACC TTC CGC CTC AAG ACT CGC AGC TGG GCT GGG GAG CGG AGC CGG    1740
Lys Thr Phe Arg Leu Lys Thr Arg Ser Trp Ala Gly Glu Arg Ser Arg
                545                 550                 555

CGG GAG CTC TGT AGC CGG CTG CAG GAC CAG TGAGGGGCCT GCGCCAGTCC      1790
Arg Glu Leu Cys Ser Arg Leu Gln Asp Gln
                560                 565

TGCTACCTCC CTTGCCTTTC GAGGCCTGAA GCCAGCTGCC CTATGGGCCT GCCGGGCTGA  1850

GGGCCTGCTG GAGGCCTCAG GTGCTGTCCA TGGGAAAGAT GGTGTGGTGT CCTGCCTGTC  1910

TGCCCCAGCC CAGATTCCCC TGTGTCATCC CATCATTTTC CATATCCTGG TGCCCCCAC   1970

CCCTGGAAGA GCCCAGTCTG TTGAGTTAGT TAAGTTGGGT TAATACCAGC TTAAAGTCAG  2030

TATTTTGTGT CCTCCAGGAG CTTCTTGTTT CCTTGTTAGG GTTAACCCTT CATCTTCCTG  2090

TGTCCTGAAA CGCTCCAGAG CTAAACTCCT TCCTGGCCTG AGAGTCAGCT CTCTGCCCTG  2150

TGTACTTCCC GGGCCAGGGC TGCCCCTAAT CTCTGTAGGA ACCGTGGTAT GTCTGCCATG  2210

TTGCCCCTTT CTCTTTTCCC CTTTCCTGTC CACCATACG AGCACCTCCA GCCTGAACAG   2270

AAGCTCTTAC TCTTTCCTAT TTCAGTGTTA CCTGTGTGCT TGGTCTGTTT GACTTTACGC  2330

CCATCTCAGG ACACTTCCGT AGACTGTTTA GGTTCCCCTG TCAAATATCA GTTACCCACT  2390

CGGTCCCAGT TTTGTTGCCC CAGAAAGGGA TGTTATTATC CTTGGGGGCT CCCAGGGCAA  2450

GGGTTAAGGC CTGAATCATG AGCCTGCTGG AAGCCCAGCC CCTACTGCTG TGAACCCTGG  2510

GGCCTGACTG CTCAGAACTT GCTGCTGTCT TGTTGCGGAT GGATGGAAGG TTGGATGGAT  2570

GGGTGGATGG CCGTGGATGG CCGTGGATGC GCAGTGCCTT GCATACCCAA ACCAGGTGGG  2630

AGCGTTTTGT TGAGCATGAC ACCTGCAGCA GGAATATATG TGTGCCTATT TGTGTGGACA  2690

AAAATATTTA CACTTAGGGT TTGGAGCTAT TCAAGAAGAA ATGTCACAGA AGCAGCTAAA  2750

CCAAGGACTG AGCACCCTCT GGATTCTGAA TCTCAATATG GGGCAGGGC TGTGCTTGAA   2810

GGCCCTGCTG AGTCATCTGT TAGGGCCTTG GTTCAATAAA GCACTGAGCA AGTTGAGAAA  2870

AAAAAAAAAA AAAAAA                                                   2886

(2) INFORMATION FOR SEQ ID NO: 4:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO: 4:

Met Glu Val Pro Gln Pro Glu Pro Ala Pro Gly Ser Ala Leu Ser Pro
1               5                   10                  15

Ala Gly Val Cys Gly Gly Ala Gln Arg Pro Gly His Leu Pro Gly Leu
            20                  25                  30

Leu Leu Gly Ser His Gly Leu Leu Gly Ser Pro Val Arg Ala Ala Ala
        35                  40                  45

Ser Ser Pro Val Thr Thr Leu Thr Gln Thr Met His Asp Leu Ala Gly
    50                  55                  60

Leu Gly Ser Arg Ser Arg Leu Thr His Leu Ser Leu Ser Arg Arg Ala
65                  70                  75                  80
```

```
Ser Glu Ser Ser Leu Ser Ser Glu Ser Ser Ser Asp Ala Ala
                85              90              95

Leu Cys Met Asp Ser Pro Ser Pro Leu Asp Pro His Met Ala Glu Gln
            100             105             110

Thr Phe Glu Gln Ala Ile Gln Ala Ala Ser Arg Ile Ile Arg Asn Glu
            115             120             125

Gln Phe Ala Ile Arg Arg Phe Gln Ser Met Pro Val Arg Leu Leu Gly
            130             135             140

His Ser Pro Val Leu Arg Asn Ile Thr Asn Ser Gln Ala Pro Asp Gly
145             150             155             160

Arg Arg Lys Ser Glu Ala Gly Ser Gly Ala Ala Ser Ser Ser Gly Glu
                165             170             175

Asp Lys Glu Asn Asp Gly Phe Val Phe Lys Met Pro Trp Asn Pro Thr
                180             185             190

His Pro Ser Ser Thr His Ala Leu Ala Glu Trp Ala Ser Arg Arg Glu
                195             200             205

Ala Phe Ala Gln Arg Pro Ser Ser Ala Pro Asp Leu Met Cys Leu Ser
210             215             220

Pro Asp Pro Lys Met Glu Leu Glu Glu Leu Ser Pro Leu Ala Leu Gly
225             230             235             240

Arg Phe Ser Leu Thr Pro Ala Glu Gly Asp Thr Glu Asp Asp Gly
                245             250             255

Phe Val Asp Ile Leu Glu Ser Asp Leu Lys Asp Asp Ala Val Pro
            260             265             270

Pro Gly Met Glu Ser Leu Ile Ser Ala Pro Leu Val Lys Thr Leu Glu
            275             280             285

Lys Glu Glu Glu Lys Asp Leu Val Met Tyr Ser Lys Cys Gln Arg Leu
290             295             300

Phe Arg Ser Pro Ser Met Pro Cys Ser Val Ile Arg Pro Ile Leu Lys
305             310             315             320

Arg Leu Glu Arg Pro Gln Asp Arg Asp Thr Pro Val Gln Asn Lys Arg
                325             330             335

Arg Arg Ser Val Thr Pro Pro Glu Glu Gln Gln Glu Ala Glu Glu Pro
                340             345             350

Lys Ala Arg Ala Leu Arg Ser Lys Ser Leu Cys His Asp Glu Ile Glu
                355             360             365

Asn Leu Leu Asp Ser Asp His Arg Glu Leu Ile Gly Asp Tyr Ser Lys
            370             375             380

Ala Phe Leu Leu Gln Thr Val Asp Gly Lys His Gln Asp Leu Lys Tyr
385             390             395             400

Ile Ser Pro Glu Thr Met Val Ala Leu Leu Thr Gly Lys Phe Ser Asn
                405             410             415

Ile Val Asp Lys Phe Val Ile Val Asp Cys Arg Tyr Pro Tyr Glu Tyr
            420             425             430

Glu Gly Gly His Ile Lys Thr Ala Val Asn Leu Pro Leu Glu Arg Asp
            435             440             445

Ala Glu Ser Phe Leu Leu Lys Ser Pro Ile Ala Pro Cys Ser Leu Asp
450             455             460

Lys Arg Val Ile Leu Ile Phe His Cys Glu Phe Ser Ser Glu Arg Gly
465             470             475             480

Pro Arg Met Cys Arg Phe Ile Arg Glu Arg Asp Arg Ala Val Asn Asp
                485             490             495
```

```
Tyr Pro Ser Leu Tyr Pro Glu Met Tyr Ile Leu Lys Gly Gly Tyr
            500                 505                 510

Lys Glu Phe Phe Pro Gln His Pro Asn Phe Cys Glu Pro Gln Asp Tyr
        515                 520                 525

Arg Pro Met Asn His Glu Ala Phe Lys Asp Glu Leu Lys Thr Phe Arg
    530                 535                 540

Leu Lys Thr Arg Ser Trp Ala Gly Glu Arg Ser Arg Glu Leu Cys
545                 550                 555                 560

Ser Arg Leu Gln Asp Gln
                565

(2) INFORMATION FOR SEQ ID NO: 5:

(i) SEQUENCE CHARACTERISTICS:
        (A) LENGTH: 2062 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 211..1631

(xi) SEQUENCE DESCRIPTION: SEQ ID NO: 5:
```

| | |
|---|---|
| CAGGAAGACT CTGAGTCCGA CGTTGGCCTA CCCAGTCGGA AGGCAGAGCT GCAATCTAGT | 60 |
| TAACTACCTC CTTTCCCCTA GATTTCCTTT CATTCTGCTC AAGTCTTCGC CTGTGTCCGA | 120 |
| TCCCTATCTA CTTTCTCTCC TCTTGTAGCA AGCCTCAGAC TCCAGGCTTG AGCTAGGTTT | 180 |

```
TGTTTTTCTC CTGGTGAGAA TTCGAAGACC ATG TCT ACG GAA CTC TTC TCA TCC    234
                                  Met Ser Thr Glu Leu Phe Ser Ser
                                    1               5

ACA AGA GAG GAA GGA AGC TCT GGC TCA GGA CCC AGT TTT AGG TCT AAT    282
Thr Arg Glu Glu Gly Ser Ser Gly Ser Gly Pro Ser Phe Arg Ser Asn
        10                  15                  20

CAA AGG AAA ATG TTA AAC CTG CTC CTG GAG AGA GAC ACT TCC TTT ACC    330
Gln Arg Lys Met Leu Asn Leu Leu Leu Glu Arg Asp Thr Ser Phe Thr
 25                  30                  35                  40

GTC TGT CCA GAT GTC CCT AGA ACT CCA GTG GGC AAA TTT CTT GGT GAT    378
Val Cys Pro Asp Val Pro Arg Thr Pro Val Gly Lys Phe Leu Gly Asp
                45                  50                  55

TCT GCA AAC CTA AGC ATT TTG TCT GGA GGA ACC CCA AAA TGT TGC CTC    426
Ser Ala Asn Leu Ser Ile Leu Ser Gly Gly Thr Pro Lys Cys Cys Leu
            60                  65                  70

GAT CTT TCG AAT CTT AGC AGT GGG GAG ATA ACT GCC ACT CAG CTT ACC    474
Asp Leu Ser Asn Leu Ser Ser Gly Glu Ile Thr Ala Thr Gln Leu Thr
        75                  80                  85

ACT TCT GCA GAC CTT GAT GAA ACT GGT CAC CTG GAT TCT TCA GGA CTT    522
Thr Ser Ala Asp Leu Asp Glu Thr Gly His Leu Asp Ser Ser Gly Leu
 90                  95                 100

CAG GAA GTG CAT TTA GCT GGG ATG AAT CAT GAC CAG CAC CTA ATG AAA    570
Gln Glu Val His Leu Ala Gly Met Asn His Asp Gln His Leu Met Lys
105                 110                 115                 120

TGT AGC CCA GCA CAG CTT CTT TGT AGC ACT CCG AAT GGT TTG GAC CGT    618
Cys Ser Pro Ala Gln Leu Leu Cys Ser Thr Pro Asn Gly Leu Asp Arg
                125                 130                 135

GGC CAT AGA AAG AGA GAT GCA ATG TGT AGT TCA TCT GCA AAT AAA GAA    666
Gly His Arg Lys Arg Asp Ala Met Cys Ser Ser Ser Ala Asn Lys Glu
            140                 145                 150

AAT GAC AAT GGA AAC TTG GTG GAC AGT GAA ATG AAA TAT TTG GGC AGT    714
```

```
                    -continued

Asn Asp Asn Gly Asn Leu Val Asp Ser Glu Met Lys Tyr Leu Gly Ser
        155                 160                 165

CCC ATT ACT ACT GTT CCA AAA TTG GAT AAA AAT CCA AAC CTA GGA GAA      762
Pro Ile Thr Thr Val Pro Lys Leu Asp Lys Asn Pro Asn Leu Gly Glu
    170                 175                 180

GAC CAG GCA GAA GAG ATT TCA GAT GAA TTA ATG GAG TTT TCC CTG AAA      810
Asp Gln Ala Glu Glu Ile Ser Asp Glu Leu Met Glu Phe Ser Leu Lys
185                 190                 195                 200

GAT CAA GAA GCA AAG GTG AGC AGA AGT GGC CTA TAT CGC TCC CCG TCG      858
Asp Gln Glu Ala Lys Val Ser Arg Ser Gly Leu Tyr Arg Ser Pro Ser
                205                 210                 215

ATG CCA GAG AAC TTG AAC AGG CCA AGA CTG AAG CAG GTG GAA AAA TTC      906
Met Pro Glu Asn Leu Asn Arg Pro Arg Leu Lys Gln Val Glu Lys Phe
            220                 225                 230

AAG GAC AAC ACA ATA CCA GAT AAA GTT AAA AAA AAG TAT TTT TCT GGC      954
Lys Asp Asn Thr Ile Pro Asp Lys Val Lys Lys Lys Tyr Phe Ser Gly
        235                 240                 245

CAA GGA AAG CTC AGG AAG GGC TTA TGT TTA AAG AAG ACA GTC TCT CTG     1002
Gln Gly Lys Leu Arg Lys Gly Leu Cys Leu Lys Lys Thr Val Ser Leu
    250                 255                 260

TGT GAC ATT ACT ATC ACT CAG ATG CTG GAG GAA GAT TCT AAC CAG GGG     1050
Cys Asp Ile Thr Ile Thr Gln Met Leu Glu Glu Asp Ser Asn Gln Gly
265                 270                 275                 280

CAC CTG ATT GGT GAT TTT TCC AAG GTA TGT GCG CTG CCA ACC GTG TCA     1098
His Leu Ile Gly Asp Phe Ser Lys Val Cys Ala Leu Pro Thr Val Ser
                285                 290                 295

GGG AAA CAC CAA GAT CTG AAG TAT GTC AAC CCA GAA ACA GTG GCT GCC     1146
Gly Lys His Gln Asp Leu Lys Tyr Val Asn Pro Glu Thr Val Ala Ala
            300                 305                 310

TTA CTG TCG GGG AAG TTC CAG GGT CTG ATT GAG AAG TTT TAT GTC ATT     1194
Leu Leu Ser Gly Lys Phe Gln Gly Leu Ile Glu Lys Phe Tyr Val Ile
        315                 320                 325

GAT TGT CGC TAT CCA TAT GAG TAT CTG GGA GGA CAC ATC CAG GGA GCC     1242
Asp Cys Arg Tyr Pro Tyr Glu Tyr Leu Gly Gly His Ile Gln Gly Ala
    330                 335                 340

TTA AAC TTA TAT AGT CAG GAA GAA CTG TTT AAC TTC TTT CTG AAG AAG     1290
Leu Asn Leu Tyr Ser Gln Glu Glu Leu Phe Asn Phe Phe Leu Lys Lys
345                 350                 355                 360

CCC ATC GTC CCT TTG GAC ACC CAG AAG AGA ATA ATC ATC GTG TTC CAC     1338
Pro Ile Val Pro Leu Asp Thr Gln Lys Arg Ile Ile Ile Val Phe His
                365                 370                 375

TGT GAA TTC TCC TCA GAG AGG GGC CCC CGA ATG TGC CGC TGT CTG CGT     1386
Cys Glu Phe Ser Ser Glu Arg Gly Pro Arg Met Cys Arg Cys Leu Arg
            380                 385                 390

GAA GAG GAC AGG TCT CTG AAC CAG TAT CCT GCA TTG TAC TAC CCA GAG     1434
Glu Glu Asp Arg Ser Leu Asn Gln Tyr Pro Ala Leu Tyr Tyr Pro Glu
        395                 400                 405

CTA TAT ATC CTT AAA GGC GGC TAC AGA GAC TTC TTT CCA GAA TAT ATG     1482
Leu Tyr Ile Leu Lys Gly Gly Tyr Arg Asp Phe Phe Pro Glu Tyr Met
    410                 415                 420

GAA CTG TGT GAA CCA CAG AGC TAC TGC CCT ATG CAT CAT CAG GAC CAC     1530
Glu Leu Cys Glu Pro Gln Ser Tyr Cys Pro Met His His Gln Asp His
425                 430                 435                 440

AAG ACT GAG TTG CTG AGG TGT CGA AGC CAG AGC AAA GTG CAG GAA GGG     1578
Lys Thr Glu Leu Leu Arg Cys Arg Ser Gln Ser Lys Val Gln Glu Gly
                445                 450                 455

GAG CGG CAG CTG CGG GAG CAG ATT GCC CTT CTG GTG AAG GAC ATG AGC     1626
Glu Arg Gln Leu Arg Glu Gln Ile Ala Leu Leu Val Lys Asp Met Ser
            460                 465                 470
```

```
CCA TG ATAACATTCC AGCCACTGGC TGCTAACAAG TCACCAAAAA GACACTGCAG    1681
Pro

AAACCCTGAG CAGAAAGAGG CCTTCTGGAT GGCCAAACCC AAGATTATTA AAAGATGTCT    1741

CTGCAAACCA ACAGGCTACC AACTTGTATC CAGGCCTGGG AATGGATTAG GTTTCAGCAG    1801

AGCTGAAAGC TGGTGGCCAG AGTCCTGGAG CTGGCTCTAT AAGGCAGCCT TGAGTGCATA    1861

GAGATTTGTA TTGGTTCAGG GAACTCTGGC ATTCCTTTTC CCAACTCCTC ATGTCTTCTC    1921

ACAAGCCAGC CAACTCTTTC TCTCTGGGCT TCGGGCTATG CAAGAGCGTT GTCTACCTTC    1981

TTTCTTTGTA TTTTCCTTCT TTGTTTCCCC CTCTTTCTTT TTTAAAAATG GAAAAATAAA    2041

CACTACAGAA TGAGAAAAAA A    2062
```

(2) INFORMATION FOR SEQ ID NO: 6:

(i) SEQUENCE CHARACTERISTICS:
        (A) LENGTH: 473 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ser Thr Glu Leu Phe Ser Ser Thr Arg Glu Glu Gly Ser Gly
 1               5                  10                  15

Ser Gly Pro Ser Phe Arg Ser Asn Gln Arg Lys Met Leu Asn Leu Leu
                20                  25                  30

Leu Glu Arg Asp Thr Ser Phe Thr Val Cys Pro Asp Val Pro Arg Thr
            35                  40                  45

Pro Val Gly Lys Phe Leu Gly Asp Ser Ala Asn Leu Ser Ile Leu Ser
        50                  55                  60

Gly Gly Thr Pro Lys Cys Cys Leu Asp Leu Ser Asn Leu Ser Ser Gly
 65                 70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Ser Met Pro Glu Asn Leu Asn Arg Pro
    210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270
```

-continued

```
Leu Glu Glu Asp Ser Asn Gln Gly His Leu Ile Gly Asp Phe Ser Lys
            275                 280                 285
Val Cys Ala Leu Pro Thr Val Ser Gly Lys His Gln Asp Leu Lys Tyr
    290                 295                 300
Val Asn Pro Glu Thr Val Ala Ala Leu Leu Ser Gly Lys Phe Gln Gly
305                 310                 315                 320
Leu Ile Glu Lys Phe Tyr Val Ile Asp Cys Arg Tyr Pro Tyr Glu Tyr
                325                 330                 335
Leu Gly Gly His Ile Gln Gly Ala Leu Asn Leu Tyr Ser Gln Glu Glu
            340                 345                 350
Leu Phe Asn Phe Phe Leu Lys Lys Pro Ile Val Pro Leu Asp Thr Gln
            355                 360                 365
Lys Arg Ile Ile Ile Val Phe His Cys Glu Phe Ser Ser Glu Arg Gly
    370                 375                 380
Pro Arg Met Cys Arg Cys Leu Arg Glu Glu Asp Arg Ser Leu Asn Gln
385                 390                 395                 400
Tyr Pro Ala Leu Tyr Tyr Pro Glu Leu Tyr Ile Leu Lys Gly Gly Tyr
                405                 410                 415
Arg Asp Phe Phe Pro Glu Tyr Met Glu Leu Cys Glu Pro Gln Ser Tyr
                420                 425                 430
Cys Pro Met His His Gln Asp His Lys Thr Glu Leu Leu Arg Cys Arg
            435                 440                 445
Ser Gln Ser Lys Val Gln Glu Gly Glu Arg Gln Leu Arg Glu Gln Ile
    450                 455                 460
Ala Leu Leu Val Lys Asp Met Ser Pro
465                 470
```